United States Patent
Tashman et al.

(10) Patent No.: US 9,538,940 B2
(45) Date of Patent: Jan. 10, 2017

(54) INTELLIGENT ALGORITHMS FOR TRACKING THREE-DIMENSIONAL SKELETAL MOVEMENT FROM RADIOGRAPHIC IMAGE SEQUENCES

(71) Applicant: University of Pittsburgh—Of the Commonwealth System of Higher Education, Pittsburgh, PA (US)

(72) Inventors: Scott Tashman, Pittsburgh, PA (US); Georgeta-Elisabeta Marai, Pittsburgh, PA (US); Md Abedul Haque, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 250 days.

(21) Appl. No.: 14/397,418

(22) PCT Filed: May 2, 2013

(86) PCT No.: PCT/US2013/039290
§ 371 (c)(1),
(2) Date: Oct. 27, 2014

(87) PCT Pub. No.: WO2013/166299
PCT Pub. Date: Nov. 7, 2013

(65) Prior Publication Data
US 2015/0094564 A1    Apr. 2, 2015

Related U.S. Application Data

(60) Provisional application No. 61/642,127, filed on May 3, 2012.

(51) Int. Cl.
*A61B 5/11* (2006.01)
*A61B 6/00* (2006.01)
(Continued)

(52) U.S. Cl.
CPC ............ *A61B 5/1128* (2013.01); *A61B 6/12* (2013.01); *A61B 6/466* (2013.01); *A61B 6/505* (2013.01);
(Continued)

(58) Field of Classification Search
CPC ....... A61B 5/1128; A61B 5/4528; A61B 6/12; A61B 6/466; A61B 6/486; A61B 6/505; A61B 6/5205; A61B 6/5217; A61B 6/563; G06T 2207/10116; G06T 2207/10121; G06T 2207/10124; G06T 2207/20016; G06T 2207/30008; G06T 7/2046
See application file for complete search history.

(56) References Cited

U.S. PATENT DOCUMENTS

| | | |
|---|---|---|
| 5,099,859 A | 3/1992 | Bell |
| 2009/0080598 A1 | 3/2009 | Tashman et al. |
| 2009/0299477 A1 | 12/2009 | Clayton et al. |

FOREIGN PATENT DOCUMENTS

| | | |
|---|---|---|
| JP | 2008514352 A | 5/2008 |
| WO | 2011158116 A2 | 12/2001 |

OTHER PUBLICATIONS

International Search Report, PCT/US2013/039290, Mailed Sep. 17, 2013.

*Primary Examiner* — Michael Rozanski
(74) *Attorney, Agent, or Firm* — Eckert Seamans Cherin & Mellott, LLC; Philip E. Levy

(57) ABSTRACT

Systems and methods are disclosed that improve conventional tracking and modeling methods for determining three-dimensional bone motion from sequences of radiographic images. These enhancements significantly improve the speed, reliability and accuracy for bone motion tracking. Techniques used in various embodiments include multi-bone hierarchical techniques, time coherent approaches, (Continued)

simultaneous optimization of the entire motion sequence and improved initial estimates of bone motion paths.

20 Claims, 14 Drawing Sheets

(51) Int. Cl.
  *A61B 6/12* (2006.01)
  *G06T 7/20* (2006.01)
  *A61B 5/00* (2006.01)
(52) U.S. Cl.
  CPC ............ *A61B 6/5205* (2013.01); *A61B 6/5217* (2013.01); *A61B 6/563* (2013.01); *G06T 7/2046* (2013.01); *A61B 5/4528* (2013.01); *A61B 6/486* (2013.01); *G06T 2207/10116* (2013.01); *G06T 2207/10121* (2013.01); *G06T 2207/10124* (2013.01); *G06T 2207/20016* (2013.01); *G06T 2207/30008* (2013.01)

INTELLIGENT ALGORITHMS FOR TRACKING THREE-DIMENSIONAL SKELETAL MOVEMENT FROM RADIOGRAPHIC IMAGE SEQUENCES

CROSS-REFERENCE TO RELATED APPLICATIONS

This application claims the benefit of U.S. Provisional Patent application Ser. No. 61/642,127 entitled 'INTELLIGENT ALGORITHMS FOR TRACKING THREE-DIMENSIONAL SKELETAL MOVEMENT FROM DYNAMIC STEREO-RADIOGRAPHIC IMAGE SEQUENCES' and filed May 3, 2012. The entirety of the above-noted application is incorporated by reference herein.

BACKGROUND

Orthopaedic disorders are a leading cause of disability in the U.S., with arthritis and/or spine problems adversely affecting quality of life for more than 20% of adults. With an aging population, the rate of disability from orthopaedic disorders has been increasing steadily. While advances in diagnostic imaging (including CT, MRI and ultrasound) have greatly improved the ability to detect structural changes in musculoskeletal tissues, they typically reveal little about joint function. There is evidence that abnormal mechanical joint function contributes significantly to the development and progression of many types of joint disease. There is, therefore, a significant clinical need for the widespread use of technologies that can identify subtle abnormalities in joint function that, if left untreated, can compromise long-term joint health.

Biomechanical analyses are a key tool for providing quantitative objective measures of patient status and treatment outcomes. There are two key requirements for biomechanical assessment for orthopaedic injury/disease. First, the measurements must be relevant to the affected tissues (cartilage, ligaments, etc.). This requires a high level of accuracy, since deformations in the sub-mm range can be significant. Second, the measurements must be performed under physiological loading conditions, since the mechanical behavior of joints is highly nonlinear and dependent on muscle and external loads. This necessitates testing during functional activities relevant to the target population. At the heart of most in vivo biomechanical analyses is the estimation of the position and orientation (pose) of a multi-segment rigid body model based on recordings of 3D motion sensor data (optical, electromagnetic, or inertial).

Accurate in-vivo motion tracking is an important tool for understanding articulation kinematics, musculoskeletal related diseases and the effectiveness of different treatments. For example, to correlate abnormal motion with morphological features such as inter-vertebral disc height (<3 mm in posterior space), sub-millimeter accuracy is needed to avoid errors as large as 30% in disc-deformation measurements.

Model-based methods have been developed to measure 3D bone motion with high accuracy at knee or shoulder joints; such methods employ 3D models of the bones, which they track through a sequence of dynamic x-ray images. Radiographic model-based methods are more accurate than skin marker-based methods, which suffer from errors as large as 10 mm in translation and 8° in rotation. Model-based methods can also capture dynamic motion, unlike existing three-dimensional techniques such as Computed Tomography (CT, which also features higher radiation exposure, depending on the anatomic location) or Magnetic Resonance Imaging (MRI). Finally, unlike dynamic three-dimensional techniques (e.g., Cine-PC MRI), model-based methods: (a) do not require continuous movement for long periods of time during data collection, (b) support in general large ranges of motion, and (c) pose fewer restrictions during imaging (due to physical constraints imposed by CT and MRI imaging systems), thus leading to loadings more similar to most everyday movements. Given the advantages of model-based tracking, systems implementing model-based methods are utilized in various forms at several different academic institutions and medical research centers; the basic imaging hardware required for biplane radiography setup costs less than one third of what a modern 3T MRI scanner costs.

A conventional model-based tracking method has three major components: 2D projection image (Digitally Reconstructed Radiograph, DRR) generation; image processing; and optimization. DRRs are generated from a 3D bone model, acquired using standard, static 3D medical imaging techniques (CT or MRI). Image processing is applied to both DRR and X-ray images. Next, an optimization method tunes the position and orientation of the bone to find the best match between the DRR and the X-ray image. The process is repeated for all frames of a motion sequence. Multiple bones have to be tracked separately in the existing (i.e., single-bone) model-based methods. These single-bone tracking methods do not take into consideration differences between the actual radiographic images and the DRR due to bone overlap and/or implanted hardware, which limit their applicability to complex joints such as the spine.

Conventional implementations of 3D model-based tracking methods all suffer from the same critical issues. The existing tracking processes are extremely labor-intensive, requiring many (up to 30) hours of labor for every hour spent collecting data. Furthermore, a high level of expertise is required to generate trustworthy results. For this reason, the tracking task cannot be reliably outsourced or delegated to a crowd-sourcing approach such as the mechanical turk. Accuracy and reliability, especially for the more automated algorithms, are inconsistent and user-dependent. Simultaneous acquisition of a pair of radiographic images is a prerequisite for all systems claiming high 3D accuracy, but this requirement creates significant image quality problems due to scatter radiation (a widely known issue for biplane radiographic imaging, which can become intractable for imaging the thicker parts of the body such as hips or the lumbar spine). It is also often difficult or impossible to obtain two radiographic views that avoid bone overlap in the images, which also degrades imaging matching performance using conventional tracking approaches. Surgically inserted hardware further decreases tracking accuracy and robustness. These limitations have thus far restricted application of this technology to research studies, since the time and cost for data analysis is prohibitive for clinical use.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises a technology that improves conventional methods by incorporating enhancements that significantly improve the speed, reliability and accuracy for bone motion tracking. These innovations can advance dynamic radiographic 3D imaging from its current status as a research tool to a clinically viable diagnostic application.

This disclosure describes enhanced approaches for determining the motion of the musculoskeletal system from a series of X-ray images (e.g., stereo or biplane radiographic images, etc.). These images could be generated by a variety of different imaging hardware configurations. Applications for this technology include (but are not limited to) assessment and diagnosis of musculoskeletal disorders, bone, ligament and joint injury, derangements of the spine and osteoarthritis.

One basic premise for tracking bone motion is a model-based tracking approach that matches radiographic images to a known bone shape. 3D models of the bones of interest are obtained using conventional imaging (CT or MRI scans). A virtual model of the stereo-radiographic imaging system is generated using the precise locations of the radiographic sources and image detectors (which can be determined automatically by imaging a calibration object of known dimensions).

Simulated x-rays are passed through the bone model to produce a pair of digitally reconstructed radiographs (DRR's) on the image plane. By manipulating the bone model within the virtual radiographic system, pairs of DRR's can be generated for any bone position. By calculating image similarity measures between the actual radiographic image pairs and the DRR's, the virtual bone position and orientation can be adjusted (manually or by an optimization algorithm) to identify the position that provides the greatest match, thus determining the position of the actual bone in space. This process is repeated for each pair of images in the motion sequence, and repeated again for each bone of interest to yield the 3D position of the joint for the entire movement.

In some aspects, the innovation can include a system that facilitates modeling a motion of a bone. Such a system can perform modeling based on a three-dimensional (3D) model of the bone and the one or more neighboring bones and a sequence of frames of the motion of the bone. Each frame can include one or more X-ray images of the bone and one or more neighboring bones. The system can include a multi-bone digitally reconstructed radiograph (MDRR) generation component that can generate one or more MDRRs corresponding to at least one frame of the sequence. Each MDRR can be a two-dimensional projection of the 3D model based at least in part on one or more motion parameters, and the one or more motion parameters can include an estimated position and an estimated orientation. The system can also include an optimization component that can determine one or more optimal motion parameters for each frame of the sequence based on a comparison between the one or more MDRRs with the one or more X-ray images of the at least one frame according to an objective function. The one or more optimal motion parameters can be the one or more motion parameters when the comparison maximizes the objective function, and when the comparison does not maximize the objective function, the optimization component can adjust the one or more motion parameters, the MDRR generation component can generate one or more additional MDRRs based at least in part on the one or more adjusted parameters, and the optimization component can compare the one or more additional MDRRs with the one or more X-ray images of the at least one frame according to the objective function.

In other aspects, the subject innovation can include a method that can facilitate model-based tracking of a motion of a bone. The method can include the acts of receiving a three-dimensional (3D) model of a bone and one or more neighboring bones and receiving a sequence of frames corresponding to the motion of the bone. Each frame can comprise one or more X-ray images. Additionally, there can be steps of receiving motion parameters comprising at least an estimate of position and an estimate of orientation for at least one frame of the sequence of frames, generating one or more multi-bone digitally reconstructed radiographs (MDRRs) based at least in part on the motion parameters, comparing the one or more MDRRs to the one or more X-ray images of the at least one frame according to a similarity measure; and determining whether the motion parameters are optimized based at least in part on the comparing. When the motion parameters are not optimized, the method can include a step of adjusting the motion parameters and repeating the steps of generating, comparing, and determining based at least in part on the adjusted motion parameters; and can include a step of outputting the motion parameters when the motion parameters are optimized.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
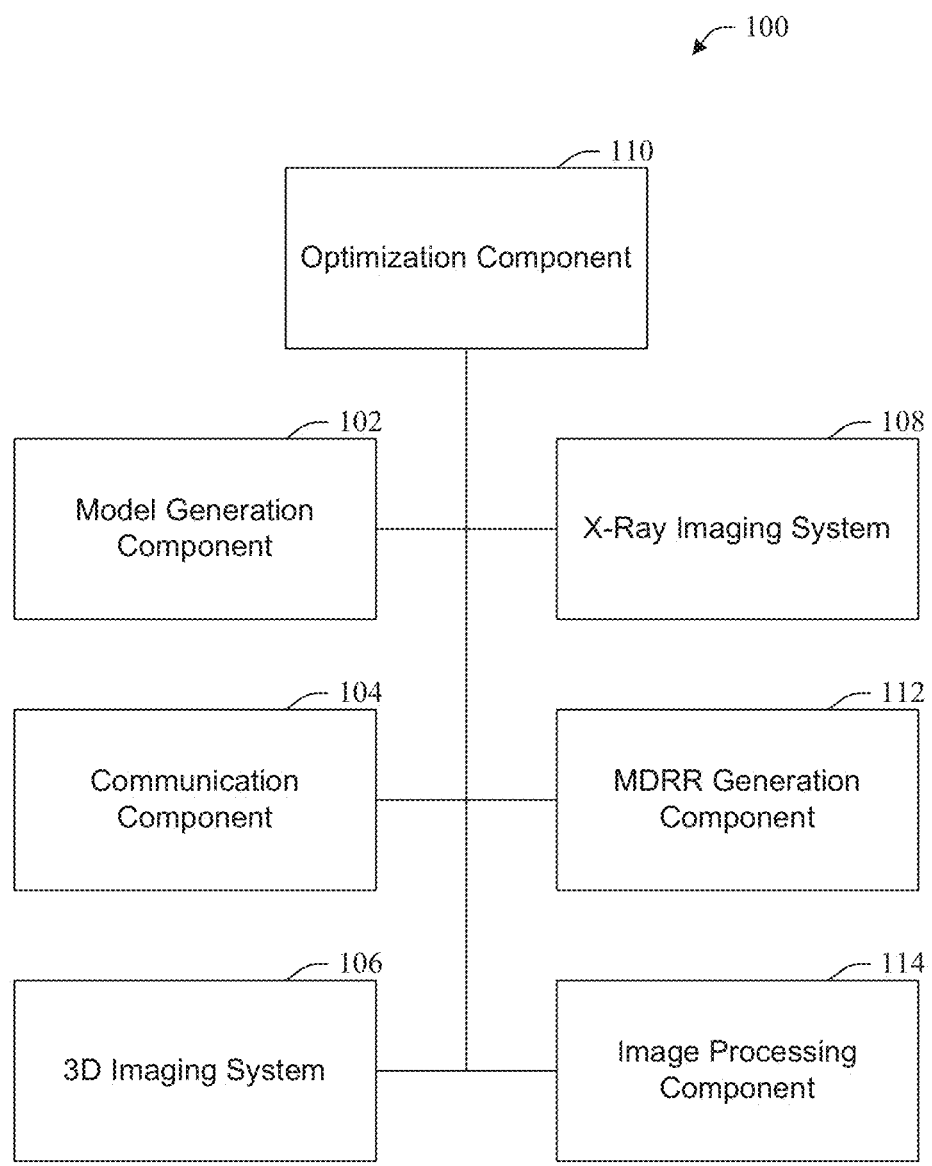
FIG. 1 illustrates a system that can facilitate motion tracking of one or more bones, in accordance with aspects of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

In aspects, the subject innovation provides systems, methods, and techniques for automatically, accurately and reliably determining the 3D motion of multi-articular joints (e.g., the cervical spine, etc.) from a series of radiographic images (e.g., stereo or biplane, etc.). These images can be acquired through a variety of different imaging hardware configurations, and the subject innovation can be used in conjunction with such images irrespective of hardware configuration. Various aspects of the subject innovation can employ a hierarchical, anatomically-aware, multi-bone approach that can take into account one or more of the complex structure of the multi-articular joints (e.g., cervical vertebrae, etc.) and overlapping bones (e.g., inter-vertebrae overlapping, etc.), as well as the temporal coherence in the imaging series. These significant innovations improve the speed, accuracy, reliability and flexibility of the tracking process. Evaluation on cervical data, discussed below, shows that approaches of the subject innovation are as accurate as the expert human-operator driven method that was previously state of the art. However, unlike the previously used method, the hierarchical approach disclosed herein can be automatic and robust even in the presence of implanted hardware, with accuracy that is user-independent. Therefore, systems and methods of the subject innovation have solid potential for clinical use to evaluate the effectiveness of surgical interventions.

Referring initially to the drawings, FIG. 1 illustrates a system 100 that can facilitate motion tracking of one or more bones, in accordance with aspects of the innovation. A model generation component 102 can generate a three-dimensional (3D) model of the one or more bones. This model can be based at least in part on imaging data, e.g., segmented imaging data, which can be received (e.g., remotely, etc.) via a communication component 104 or can be received directly from a 3D imaging system (e.g., computed tomography (CT) or magnetic resonance imaging (MRI), etc.) 106 or associated imaging processing and segmentation systems. Based on a sequence of X-ray images captured by X-ray imaging system 108 (which can be of substantially any type described herein, e.g., biplane, stereo, etc.) or received via communication component 104, optimization component 110 can determine a set of optimized motion parameters (e.g., position, orientation, etc. as a function of time or for the various frames, etc.) that model the motion captured by the sequence of X-ray images via substantially any of the techniques described herein, e.g., frame-by-frame techniques, four dimensional techniques, etc.

Optimization component 110 can receive or determine initial parameters (e.g., an initial estimation of position and orientation, etc.) in a variety of ways, depending on the embodiment of system 100. For example, initial motion parameters in a frame-by-frame motion tracking embodiment can be input by a user for one or more frames, or can be determined automatically using techniques discussed herein (e.g., temporal coherence techniques, employing a tracking hierarchy of bones such as discussed herein, for example, a coarse-to-smooth tracking that can progress from one or more fast approximation to refined highly accurate solutions, etc.) for one or more frames; in some embodiments, user input can provide initial parameters for the first few (e.g., two, etc.) frames, while initial parameters for other frames can be determined automatically. In an example employing four dimensional techniques discussed herein, initial parameters can take the form of a Bayesian prior that can be automatically determined based on externally captured motion data from auxilliary measurement systems employing optical, inertial or other available technologies (e.g., received via communication component 104, etc.). Based on the initial parameters and optimization technique employed in the particular embodiment of system 100, determination of optimized motion parameters can proceed in a variety of ways, as described herein. For example, in some frame-by-frame embodiments, for each frame, initial parameters can be determined as described herein, and based on the initial parameters, multi-bone Digitally Reconstructed Radiograph (MDRR) generation component 112 can generate one or more two dimensional (2D) projections of the 3D model by projecting simulated X-rays through the model bone of the 3D model and one or more neighboring bones from virtual locations corresponding to the X-ray sources used to obtain the sequence of X-ray images. These one or more MDRRs and the corresponding image(s) for the frame of the sequence of X-rays can be sent to image processing component 112, which can perform one or more image processing techniques described herein (e.g., Gaussian filter, Sobel filter, weighted averaging, etc.) to produce processed MDRRs and processed X-ray images. These processed images can be compared by optimization component 110 (e.g., according to an objective function, etc.) to determine whether the parameters used to generate the one or more MDRRs are optimal, or whether these parameters should be adjusted and a new one or more MDRRs should be generated based on the adjusted parameters. Embodiments employing frame-by-frame techniques can proceed to the next frame, using techniques described herein. Embodiments utilizing four dimensional optimization techniques can optimize the entire trajectory simultaneously, as described in greater detail below.

It is to be appreciated that not every component discussed in connection with system 100 is required. As one of many examples, 3D imaging data can be received via communication component 104 such that 3D imaging system 106 is not required, or vice versa.

Figure 2:
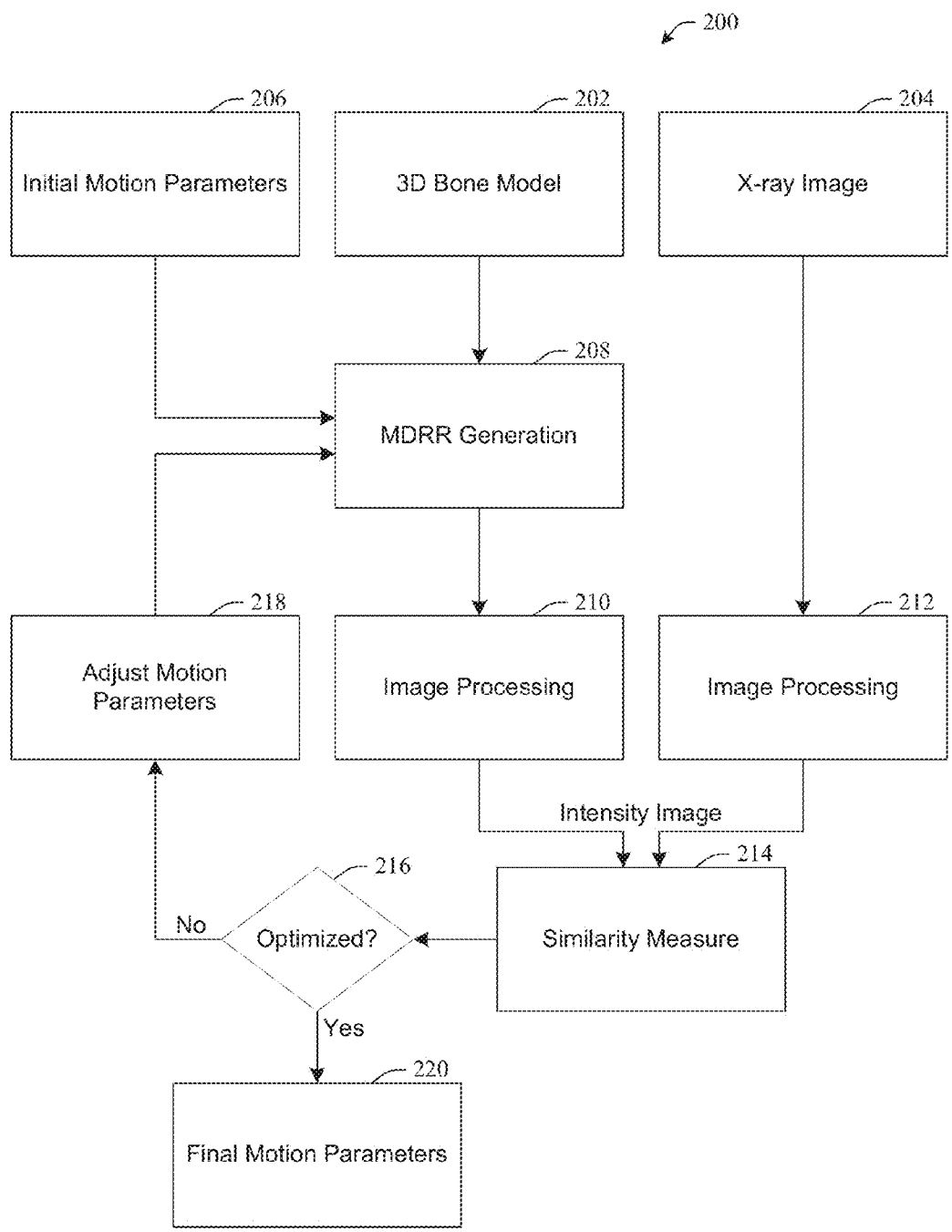
FIG. 2 illustrates a method that facilitates model-based tracking of bone motion, in accordance with aspects of the subject innovation.

FIG. 2 illustrates a method 200 that facilitates model-based tracking of bone motion, in accordance with aspects of the subject innovation. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

Method 200 can begin at step 202 by receiving or constructing a 3D model of a bone, such as a bone of a multi-articular joint (e.g., cervical vertebrae, etc.), along with one or more neighboring bones. In aspects, such a model can be constructed as described herein, such as by receiving or capturing imaging data (e.g., CT, MRI, etc.) associated with the bone (e.g., of a multi-articular joint, etc), and constructing a 3D model of the bone based at least in part on the imaging data (e.g., based on segmented imaging data, etc.). At 204, a motion sequence of X-ray images of the bone (e.g., of the multi-articular joint, etc.) and one or more neighboring bones can be captured or received (e.g., a time series of pairs of biplane or stereo-radiographic images, etc.). At 206, initial motion parameters can be calculated or received, as described in greater detail herein. At 208, a 2D projection (multi-bone Digitally Reconstructed Radiograph, or MDRR) of the 3D model can be generated via ray-casting volume rendering through neighboring bones and based at least in part on motion parameters (either initial or adjusted) for a current X-ray frame of the motion sequence. Then at 210 and 212, image processing can be performed on the MDRR (at 210) and X-ray (at 212) images, e.g., to reduce noise and enhance edges, etc.

Next, at 214, the processed MDRR and X-ray images can be compared, e.g., based on a similarity measure. Based on the comparison (e.g., similarity measure, etc.), at 216, a determination can be made as to whether the motion parameters (e.g., the bone position and orientation, etc.) are optimized. If not, then motion parameters can be adjusted at 220, and the method can return to 208 to generate a new MDRR based at least in part on the adjusted motion parameters. If, however, a determination was made at 216 that the MDRR was optimized, then at 218 final motion parameters can be output for the frame. After step 218, the method can repeat for a next frame of the motion sequence, and when all frames have been modeled for a given bone, can repeat through method 200 for each frame, and for each frame for any other bones to be modeled (e.g., other cervical vertebrae or other bones of a multi-articular joint, etc.).

Various techniques discussed herein (e.g., temporal coherence, pairwise optimization, biased singleton refinement, neighbor-constrained refinement, etc.) can be used to estimate initial motion parameters for frames in the sequence. It is to be appreciated that in various implementations of the subject innovation, a four dimensional optimization can be employed instead of a frame-by-frame optimization, to solve for all frames simultaneously (e.g., via spline or other parametric curve techniques described herein, etc.). Additionally, in some aspects, the analytical steps (e.g., model and MDRR generation, image processing, optimization, etc.) can occur remotely from imaging steps (e.g., CT or MRI imaging, capture of X-ray image sequence, any optical imaging (e.g., as used for a Bayesian prior, etc.), etc.), while in other embodiments these steps can occur at the same location.

What follows is a more detailed discussion of certain systems, methods, and apparatuses associated with aspects of the subject innovation. To aid in the understanding of aspects of the subject innovation, theoretical analysis and experimental results associated with specific experiments that were conducted are discussed herein. However, although for the purposes of obtaining the results discussed herein, specific choices were made as to the selection of various aspects of the experiments and associated setups—such as choice of imaging systems and anatomical region—the systems and methods described herein can be employed in other contexts, as well. For example, various aspects of the subject innovation can be utilized to assess other bone and joint motion, such as knees, shoulders, hips, other spinal regions, etc. In some embodiments, different analytical techniques (e.g., image processing, optimization, etc.) can be selected or employed than those used in the experiments discussed herein, and may produce different results, as explained in greater detail below.

The limitations of conventional implementations of 3D model-based tracking have thus far restricted application of this technology to research studies, since the time and cost for data analysis is prohibitive for clinical use. In contrast to conventional systems, however, aspects of the subject innovation can employ an automated intelligent, hierarchical model-based method to track with sub-millimeter accuracy the 3D motion of multi-articular joints, such as cervical vertebrae, from imaging data (e.g., dynamic biplane radiographs, etc.). The specific focus of experimental work discussed below was automation while matching the accuracy of human expert operators on difficult, clinical cervical spine data. However, it is to be appreciated that the subject innovation can be employed in other contexts as well; similar challenges exist in accurate tracking of all multi-articular joints, many of which feature significant bony or hardware overlap (e.g. the hip, shoulder, wrist or ankle).

The basic premise for tracking bone motion is a model-based tracking approach that matches radiographic images to a known bone shape. 3D models of the bones of interest can be obtained using conventional imaging (e.g., CT or MRI scans). A virtual model of the stereo-radiographic imaging system can be generated using the precise locations of the radiographic sources and image detectors (which can be determined automatically by imaging a calibration object of known dimensions).

Figure 3:
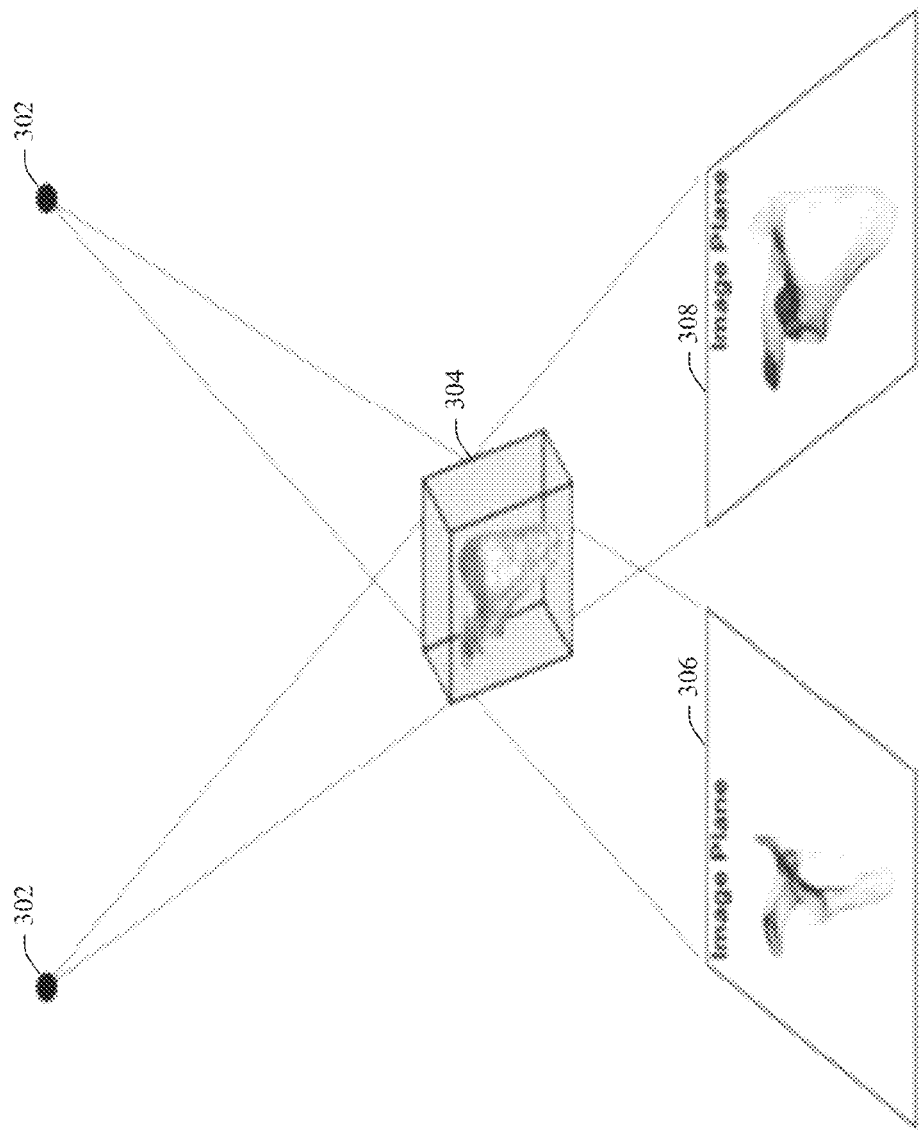
FIG. 3 shows a representation of the generation of digitally reconstructed radiographs (DRRs).

FIG. 3 shows a representation of the generation of digitally reconstructed radiographs (DRRs). Simulated x-ray sources 302, with virtual locations relative to the model bone 304 corresponding to the real sources locations relative to the actual bone, can generate simulated x-rays that can be passed through the bone model (e.g., generated from segmented CT or MRI data, etc.) to produce a pair of digitally reconstructed radiographs (DRRs) 306 and 308 on the image plane. By manipulating the bone model 304 within the virtual radiographic system, pairs of DRRs 306 and 308 can be generated for any bone position. By calculating image similarity measures between the actual radiographic image pairs and the DRRs 306 and 308, the virtual bone position and orientation can be adjusted (manually or by an optimization algorithm) to identify the position that provides the greatest match, thus determining the position of the actual bone in space. This process can be repeated for each pair of the images in the motion sequence, and repeated again for each bone of interest to yield the 3D position of the joint for the entire movement.

In conventional model-based tracking, the presence of overlapping bones (a common occurrence) reduces the quality of image matching and degrades tracking performance. Also, tracking each bone independently ignores the known characteristics of joints that constrain the relative bone movements. In contrast, the subject innovation can employ a hierarchical multi-bone model approach, in which multiple bones can be combined in a single 2D projection and simultaneously matched with the radiograph images. This approach takes advantage of the rich detail present in regions of radiographic bone overlap, which can therefore enhance, rather than degrade, tracking performance. By incorporating one or more features of the subject innovation disclosed herein, such as hierarchical, anatomically aware, multi-articular models of joints, as well as temporal coherence, tracking reliability can be further enhanced by exploiting known constraints that are defined across space and time.

The subject innovation discloses enhanced approaches (systems, methods and components) for determining the motion of the musculoskeletal system from a series of radiographic images. These images could be generated by a variety of different imaging hardware configurations, which are not specifically addressed in this disclosure, but would be appreciated by those skilled in the art. One application of the innovation employs biplane or stereo radiographic image acquisition, but systems and algorithms would also enhance tracking of bone motion from single-plane imaging. Applications for this technology include (but are not limited to) assessment and diagnosis of musculoskeletal disorders, bone, ligament and joint injury, derangements of the spine and osteoarthritis.

One premise for tracking bone motion according to the subject innovation can employ a model-based tracking approach that matches radiographic images to a known bone shape. 3D models of the bones of interest can be obtained using conventional imaging (e.g., CT or MRI scans, etc.). A virtual model of the stereo-radiographic imaging system can be generated using the precise locations of the radiographic sources and image detectors (which can be determined automatically by imaging a calibration object of known dimensions).

Simulated x-rays can be passed through the bone model to produce a pair of digitally reconstructed radiographs (DRR's) on the image plane. By manipulating the bone model within the virtual radiographic system, the system can generate pairs of DRR's for any bone position. By calculating image similarity measures between the actual radiographic image pairs and the DRR's, the virtual bone position and orientation can be adjusted (e.g., manually or by an optimization algorithm, etc.) to identify the position that provides the greatest match, thus determining the position of the actual bone in space. This process can be repeated for each pair of images in the motion sequence, and can be repeated again for each bone of interest to yield the 3D position of the joint for the entire movement. The process can work similarly, albeit with lower accuracy and reliability, if only single-plane images are available.

While conventional approaches have been described in research literature and are utilized (in various forms and with variations from the subject innovation) at several different academic institutions and medical centers, these approaches differ from the subject innovation. All of these existing implementations, for example, suffer from the same critical issues. The existing procedures are extremely labor-intensive, requiring many hours to process data from each movement. Additionally, accuracy and reliability of these conventional techniques, especially for the more automated algorithms, is inconsistent. Simultaneous acquisition of a pair of radiographic images is a prerequisite for all systems claiming high 3D accuracy, but this requirement creates significant image quality problems due to scatter radiation (a widely known issue for biplane radiographic imaging, which can become intractable for imaging thicker parts of the body such as hips or the lumbar spine). It is also often difficult, or impossible, to obtain two radiographic views that avoid bone overlap in the images, which also degrades imaging matching performance using conventional tracking approaches. These limitations have thus far limited application of this technology to research studies, since the time and cost for data analysis is prohibitive for clinical use.

Contrary to conventional systems, aspects of the subject innovation can employ one or more of the innovative techniques disclosed herein, each of which improve the speed, accuracy, reliability and/or flexibility of the tracking process. It is to be understood that each of these innovations could be applied individually or in combination to enable rapid, automated, accurate bone motion tracking and facilitate clinical applications. Multiple such innovations are discussed herein.

In aspects, the subject innovation can employ hierarchical multi-bone tracking. In conventional model-based tracking, the presence of overlapping bones (a common occurrence) reduces the quality of image matching and degrades tracking performance. Also, tracking each bone independently ignores the known characteristics of joints that constrain the relative bone movements. In aspects, the subject innovation can employ a hierarchical multi-bone model approach, in which multiple bones can be combined in a single 2D projection and simultaneously matched with the radiograph images. This approach takes advantage of the rich detail present in regions of radiographic bone overlap, which can therefore enhance (rather than degrade) tracking performance. By incorporating hierarchical, anatomically aware, multi-articular models of joints, tracking reliability can be further enhanced by exploiting known constraints that are defined between the bones. For example, bones cannot interpenetrate or separate more than a certain amount, and the range of motion for some degrees of freedom is limited for some joints. Thus, knowing the position of one bone can aid in locating the second bone by significantly reducing the search space. By accounting for bone overlap, this enhancement can facilitate rapid, accurate tracking of joint motions from image sequences that are currently considered to be of insufficient quality for automated processing. Creating a tracking hierarchy of bones (e.g., from least to most overlap)

would be especially helpful for enabling tracking of bones that would be too completely obscured for conventional single-bone tracking.

In the same or other aspects, the subject innovation can employ the incorporation of common motion constraints, paths and ranges of motion. Tracking each bone independently ignores the known characteristics of joints that constrain the relative bone movements. By incorporating hierarchical, anatomically aware, multi-articular models of joints, tracking reliability can be further enhanced by exploiting known constraints that are defined between the bones. For example, bones cannot interpenetrate or separate more than a certain amount, and the range of motion for some degrees of freedom is limited for some joints. Thus, knowing the position of one bone can aid in locating the second bone by significantly reducing the search space.

Additionally or alternatively, four-dimensional tracking techniques can be employed in conjunction with the subject innovation. If imaging sample rates are adequate, the motion paths of bones and joints can generally be considered smooth. Current tracking algorithms take only limited advantage of this fact, typically by simple extrapolation to estimate an "initial guess" for a new motion frame by extrapolating from positions of the previous frames. The innovation can employ a more enhanced approach that takes full advantage of the temporal coherence inherent to the data.

For each frame, motion relative to earlier frames can be measured, and sudden jumps in the motion measurements can be fed back to the tracking procedure to allow for on-the-fly error correction. In some aspects, rather than optimizing the position of each motion frame independently, the entire four-dimensional (4D) motion path (3D position/orientation×time) can be simultaneously optimized to provide true bone trajectories. One major advantage of this approach is that it can eliminate the requirement for simultaneous image acquisition, as images acquired from any view at any time can be matched to the trajectory. This would enable tracking from alternating 2-view imaging, which is not an option for conventional biplane tracking (which requires simultaneous image acquisition) but is the standard for clinical biplane imaging (e.g., cine-angiography) because it leads to dramatic improvements in radiographic image quality. It also facilitates reliable tracking around individual frames with unusable images (e.g., obscured by hardware, the brief interference of another limb such as a swinging arm, etc.).

Additionally, various aspects of the subject innovation can optionally employ techniques to improve tracking guidance via auxiliary motion measurement.

Radiographic tracking algorithms require a relatively good "initial guess" to converge on the correct trajectory, because the correlations between DRR's and radiographs degrade rapidly as the estimated bone position deviates from the true position, and there are many incorrect local optima that confound the search process. Much of the manual effort required by current approaches is related to determining these initial position estimates. Many laboratories already contain non-radiographic systems for measuring human movement, such as video-motion analysis systems, accelerometers, etc. Small sensors combining accelerometers, gyroscopes and magnetometers (as employed routinely in smartphones, as well as low-cost consumer motion tracking systems (e.g. Kinect by Microsoft, Inc.), are becoming widely available, affordable and easy to use, requiring minimal data processing effort.

While they cannot recreate bone motion accurately (because they rely on external landmarks/devices or images of the skin or clothing for tracking), they can provide initial trajectory estimates that can be used to guide the radiographic tracking process. This could be particularly beneficial when used in conjunction with the 4D tracking approach, since the external measurement systems would provide initial estimates for the entire motion trajectories, which would then be refined based on the radiographic tracking. Video-motion analysis (using reflective markers) could be especially beneficial for multi-bone tracking, especially if recently developed algorithms for improving bone estimates from skin markers are incorporated into the process.

These innovations do not represent simple, minor improvements over previous capabilities, but rather a fundamentally novel approach that would turn a limited-use research tool into a powerful clinical device for rapid, low-cost, dynamic assessment of musculoskeletal function. Just as cine-angiography has revolutionized diagnosis and treatment of cardiovascular disorders, widespread availability of dynamic musculoskeletal imaging could significantly improve treatment for a wide variety of orthopaedic disorders.

Systems and methods of the subject innovation can employ a novel digitally reconstructed radiograph generation procedure (multi-bone DRR, or MDRR), an image processing step, and a novel hierarchical optimization procedure. For each X-ray frame in the motion sequence, a 2D projection (MDRR) can be generated from the multiple reconstructed bone models. Next, both the X-ray and the 2D projection images can be processed to reduce noise and enhance edges. Finally, an optimization method can be employed to search through different positions and orientations of the bone models to find the best match between the MDRR and the X-ray image. The process can be repeated for all frames of a motion sequence.

While a variety of imaging hardware setups can be used in practice to acquire dynamic radiograph images and static three-dimensional bone models, experiments described herein used high-resolution X-ray images captured using a dynamic stereo X-ray (DSX) system, and 3D volumetric images of the bones of interest acquired with a high-resolution static computed tomography scanner, as discussed below.

Model-based tracking is based on the idea that an X-ray image can be computationally produced using a simplified X-ray generation model, as in equation 1:

$$I(p) = \int_L \mu(r) dr \quad (1)$$

where $I(p)$ is the intensity of the X-ray detector pixel p, $\mu(r)$ is the X-ray attenuation coefficient, and L is the projection beam from source to point p. This model assumes that the X-ray system corrects for beam divergence and that the sensors have logarithmic response.

$I(p)$ can be estimated using ray casting of the CT image and the resulting image is known as the Digitally Reconstructed Radiograph (DRR). The segmented CT (or MRI, etc.) image can serves directly as the 3D bone model.

However, in reality, the intensity of a pixel $I(p)$ not only depends on the bone of interest, but also on any other structure the beam L passes through. Thus, $I(p)$ can be thought of as integration of contributions from several different sources, as in equation 2:

$$I(p) = I_c(\text{bone of interest}) + I_c(\text{neighboring bones}) + \quad (2)$$
$$I_c(\text{metallic implants}) + I_c(\text{other bones}) + I_c(\text{soft tissue}) +$$
$$I_c(\text{unmodeled radiographic effects}) + I_c(\text{random noise})$$

where $I_c(O)$ represents contribution to pixel (x, y) due to object O. Unmodeled radiographic effects include atomic interactions such as Compton scattering.

Existing conventional bone-tracking methods assume that the contribution to a pixel intensity from all the sources except the bone itself is negligible or constant. This assumption does not hold for spine data (and other joints) where neighboring bones and implants overlap significantly. In conventional techniques, however, a single-bone DRR (SDRR) is nonetheless generated using only the model of the bone being tracked, and accounts only for the first term of equation 2, $I_c$ (bone of interest).

To account for contributions from neighboring bones and surgical implants, various aspects of the subject innovation can employ the following model for multi-bone DRR (MDRR) generation, shown in equation 3:

$$I_{MDRR}(p) = I_c(\text{bone of interest}) + I_c(\text{neighboring bones}) + I_c(\text{metallic implants}) \quad (3)$$

In this approximation, it is assumed that contribution due to non-neighboring bones (e.g. shoulder, skull) can usually be avoided by careful positioning of X-ray sources and detectors. Any contribution due to soft tissue and random noise is assumed negligible here. Although still an approximation, the resulting MDRRs have a more realistic signature in adjacent regions than the SDRRs.

Some implementations can also use knowledge of multi-segment motion and soft tissue geometry and tissue composition (e.g. from MRI) to estimate radiographic contributions from soft tissue positioning and/or scatter effects, further improving MDRR quality.

Figure 4:
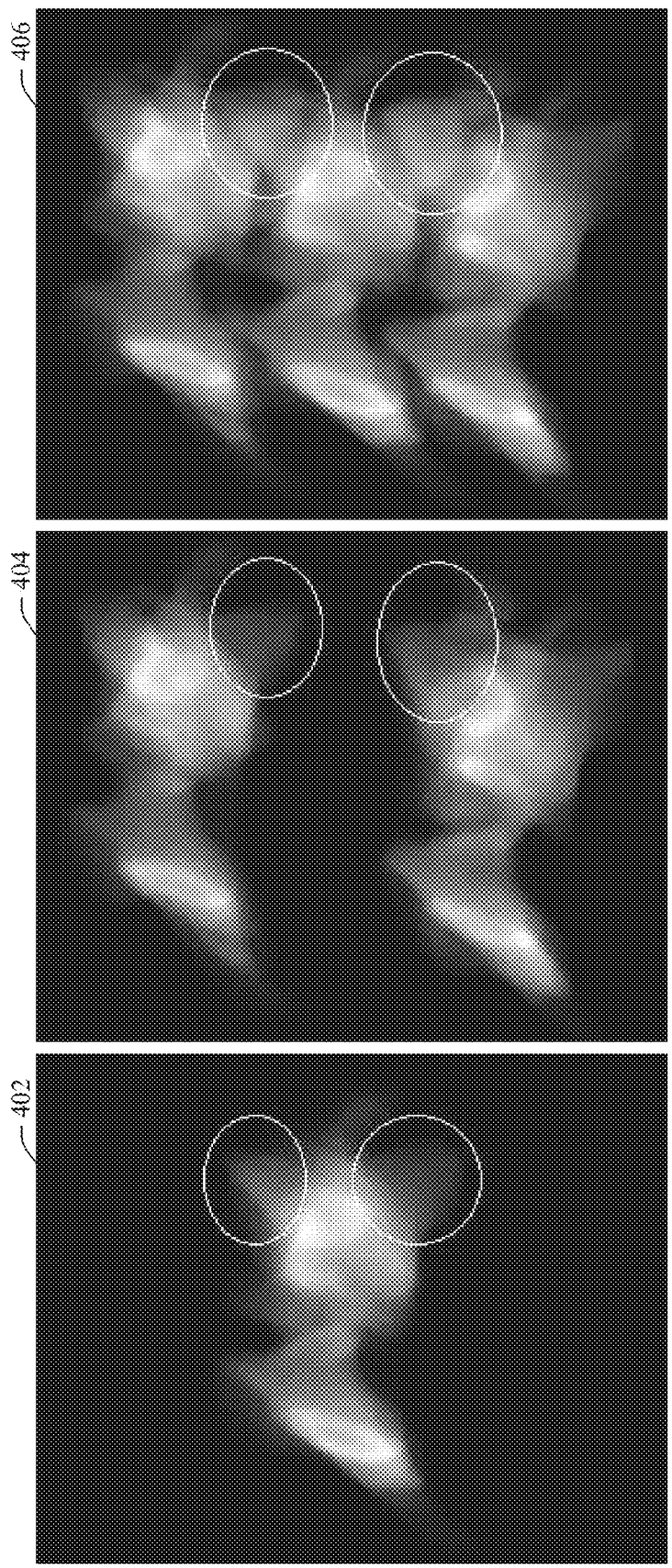
FIG. 4 shows DRR projections of the C3, C4, and C5 vertebrae, illustrating how the presence of other bones changes the signature of a bone of interest.

FIG. 4 shows DRR projections of the C3, C4, and C5 vertebrae, illustrating how the presence of other bones changes the signature of a bone of interest. Image 402 shows a single bone projection of C4, with regions of overlap with the C3 and C5 vertebrae circled. Image 404 shows C3 and C5, with the same regions of overlap again circled. In image 406, a multi-bone projection of C4 is shown with C3 and C5, again indicating the regions of overlap. As can be seen in the circled region of image 406, the presence of C3 and C5 changes the signature of C4 in the adjacent regions.

The subject innovation can use ray-casting volume rendering through multiple neighboring bones to generate MDRRs. On a single 2.0 GHz processor, such as used in experiments discussed herein, each MDRR generation required on average 100 ms. However, during bone position and orientation optimization, more than 500 MDRRs may need to be generated for each motion frame. A sequential implementation would require approximately 6 hours of computation time to track 6 vertebrae over 60 frames. To reduce the computation time, a parallel implementation of the MDRR generation process can be employed using clusters of multi-core general-purpose CPU systems, as was done in conjunction with experiments discussed herein. Parallel computations can also be performed using vector processing units, GPU (graphics processing unit) arrays or other high-performance computational architectures to further reduce processing time.

Figure 5:
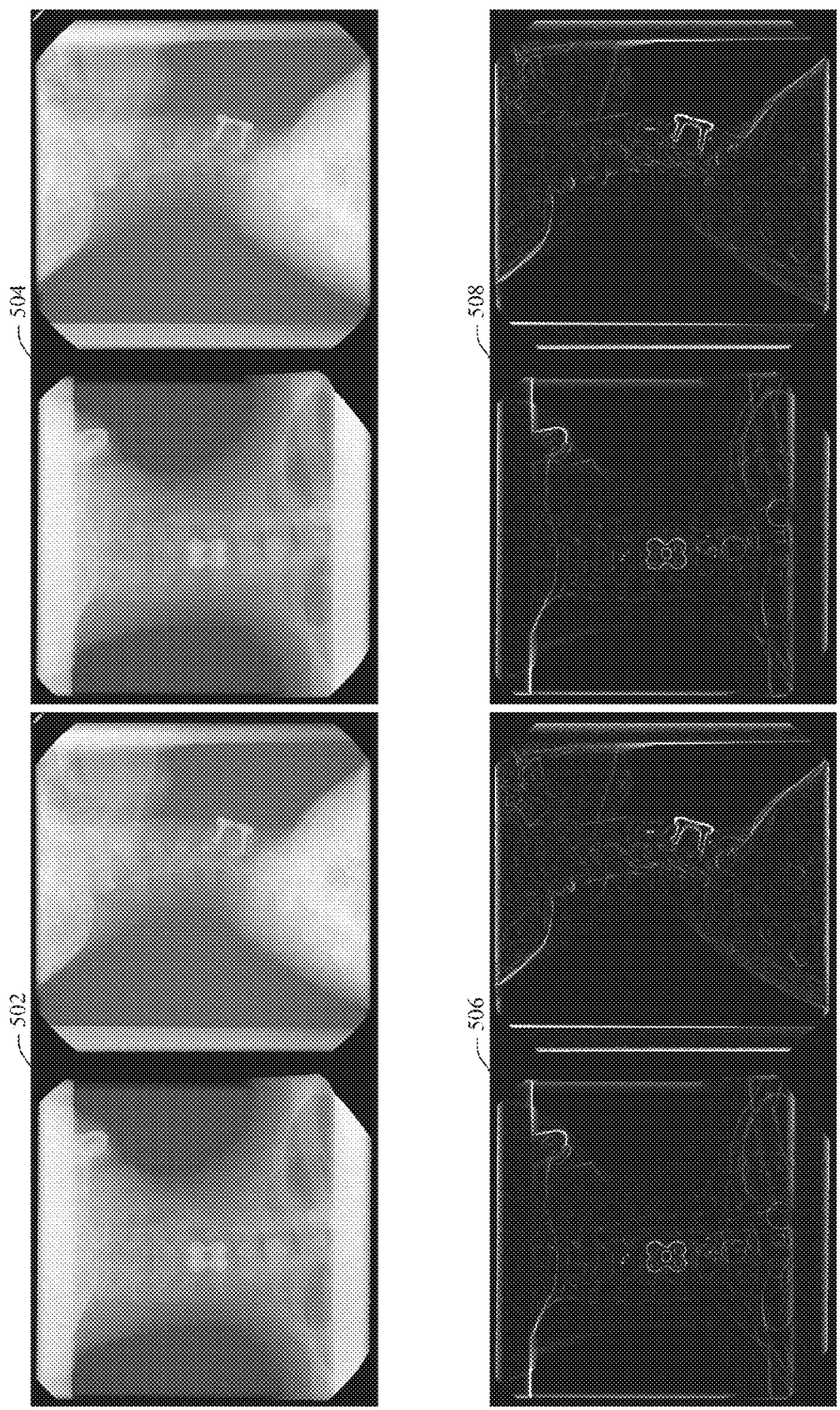
FIG. 5 hows representative images for image processing steps useable in aspects of the subject innovation.

The image processing steps and the similarity metric employed during experiments were similar to earlier studies, to facilitate isolation and investigation of the effect of MDRRs and hierarchical optimization. However, it should be apparent in light of the teachings herein that different filters, techniques, algorithms, and metrics can be used for image processing or similarity determination than those used during the experiments discussed herein. The MDRRs and the X-ray images were passed through several standard image processing steps to reduce noise and enhance edges of the images. FIG. 5 shows representative images for each of these image processing steps. Images 502 are raw, unprocessed, X-ray images, and 504 shows the corresponding Gaussian-filtered images (e.g., a 3×3 discrete Gaussian filter applied to reduce noise, etc.). Images 506 shows the results of Gaussian and Sobel filtering (e.g., a 3×3 Sobel filter applied to extract edges from the smoothed images, etc.), and images 508 show the results after applying Gaussian and Sobel filtering and taking a weighted average between the smoothed and the edge enhanced images (images 506 and 508 were contrast-enhanced for printing purposes). The weighted average of the smoothed image g and the edge-extracted image h, as shown in equation 4:

$$k(x,y) = w_0 * g(x,y) + w_1 * h(x,y) \quad (4)$$

where $w_0$ and $w_1$ were empirically determined to be, respectively, 0.1 and 0.9 for DRRs, and 0.15 and 0.85 for X-ray images.

The similarity between edge-enhanced X-ray and MDRR images was measured in the experiments using normalized correlation (r) which has been reported as one the best performing similarity metrics for high-resolution, real clinical data; however, other image similarity metrics can be used in various embodiments of the subject innovation. The normalized correlation is given by equation 5:

$$r_{(j=1,2)} = \frac{\Sigma(I_{Xray_j}(x,y) - \bar{I}_{Xray_j})(I_{MDRR_j}(x,y) - \bar{I}_{MDRR_j})}{\sqrt{\Sigma(I_{Xray_j}(x,y) - \bar{I}_{Xray_j})^2}\sqrt{\Sigma(I_{MDRR_j}(x,y) - \bar{I}_{MDRR_j})^2}} \quad (5)$$

for all pixels (x, y) such that $I_{MDRR_j}(x, y) \neq 0$. Here, j denotes the X-ray camera number of the bi-plane X-ray system. As has been previously done, correlations for two sets of X-ray and MDRR images can be multiplied to get the final matching score, shown in equation 6:

$$\text{corr}(I_{Xray_1}, I_{Xray_2}, I_{MDRR_1}, I_{MDRR_2}) = r_1 * r_2 \quad (6)$$

Alternatively, the relative weighting of the matching metrics from the two images could be adjusted based on the relative quality of the images, to improve estimates in cases where one view is partially obstructed or provides an incomplete view of the bone(s) of interest.

Figure 6:
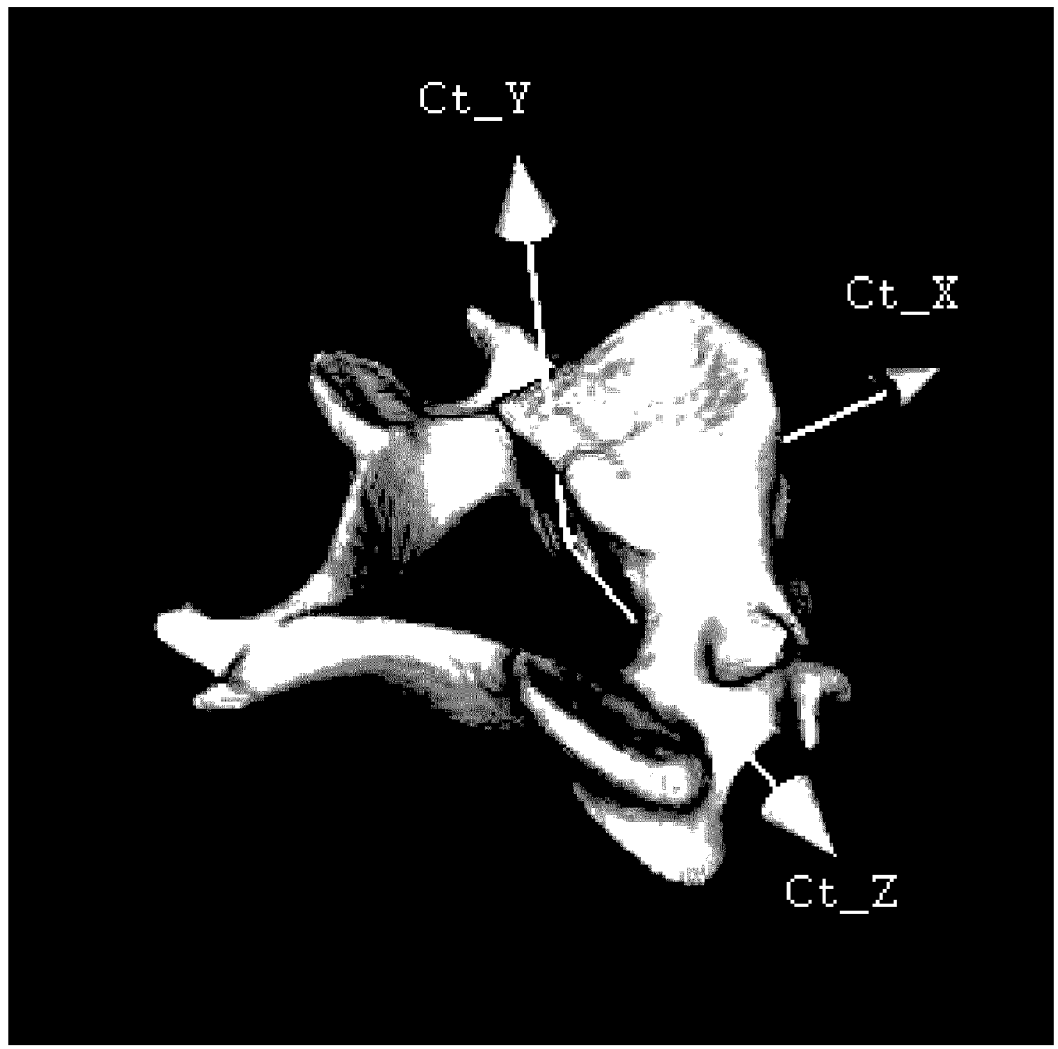
FIG. 6 illustrates a cervical vertebra and its local coordinate system.

While MDRRs have the potential to increase the accuracy and robustness of tracking, they also pose challenges in terms of the optimization of search space. The experiments employed a quasi-Newton optimization method for finding the point of the maximum matching score. Each bone i has 6 degrees of freedom, expressed in matricial form as: $M_i = (T_x, T_y, T_z, R_x, R_y, R_z)$, the concatenation of 3 translations and 3 rotations. Translations and rotations are specified with respect to a local coordinate system. FIG. 6 illustrates a cervical vertebra and its local coordinate system; the origin $(CT_x, CT_y, CT_z)$ of the local coordinate system is the center of mass of a CT object (or corresponding other imaging object, e.g., MRI, etc.), as shown in equation 7:

$$CT_{(X=x,y,z)} = \frac{\Sigma X * f(x, y, z)}{\Sigma f(x, y, z)} \quad (7)$$

Where f denotes the CT image (or corresponding other image).

The objective function for the optimization method is shown in expression 8:

$$\max_{T_x,T_y,T_z,R_x,R_y,R_z} \prod_{j=1,2} \text{corr}[I_{Xray_j}, I_{MDRR_j}(T(CTObject))] \quad (8)$$

where $T=T_x \cdot T_y \cdot T_z \cdot R_x \cdot R_y \cdot R_z \cdot T_{-CT_x} \cdot T_{-CT_y} \cdot T_{-CT_z}$ is the composite transformation matrix and j denotes the two cameras of a DSX (Dynamic Stereo X-ray) system. Maximizing the objective function of expression 8 can provide a best match between the model and the X-ray images. The above equations show optimization of a single bone; however, it can be expanded for multiple bones as necessary. In various aspects of the subject innovation, the search can be initialized by a human operator for the first two frames. For the remaining frames, initialization can be done by exploiting temporal coherence as described herein. In other aspects, external data (e.g., optical motion capture, etc.) can be used alternatively or additionally for initialization and/or trajectory modeling.

Ideally, all bones of the hierarchy would be present in the MDRR and the optimization algorithm would tackle all bones simultaneously. However, such an approach can become computationally intractable due to the large, relatively unorganized search space and to the large number of degrees of freedom (6n where n is the number of the bones). In contrast, employing temporal coherence, inter-frame and inter-bone motion priors, and a systematic hierarchical technique can reduce the search space significantly. At the same time, a hierarchical approach can allow sufficient degrees of freedom between bones to capture joint motion accurately.

Based on the above observations, the experiments employed a coarse-to-fine, multi-pass strategy. The first two passes corresponded to a coarse search for the bone location and orientation. Due to the fewer degrees of freedom and more constraints, phases 3 and 4 corresponded to a fine tuning stage; phase 4 imposed more constraints on the searching than phase 3.

In terms of relative contribution, early experiments showed that phase 1 and 3 significantly impact the registration robustness. The exclusion of phase 1 in the search method produced off-track solutions and the exclusion of phase 3 produced very poor quality solutions. Phase 2 and 4 contribute primarily to tracking accuracy. Together, the four phases complement each other and lead to a robust and accurate solution, as demonstrated by experimental results discussed herein.

Each phase used in the experiments is described in detail below using an example linear hierarchy consisting of n bones, B1 (first) through Bn (last). Let $K_i$ be the set of bones which are used to generate MDRR at the $i^{th}$ round of a given phase and $L_i=(B_j|F_k)$ be the subset of bones $B_j$ in $K_i$ which are optimized during the $i^{th}$ round of the given phase, given the fixed position and orientation of the $F_k$ bones.

Phase 1: Temporal Coherence

Figure 7:
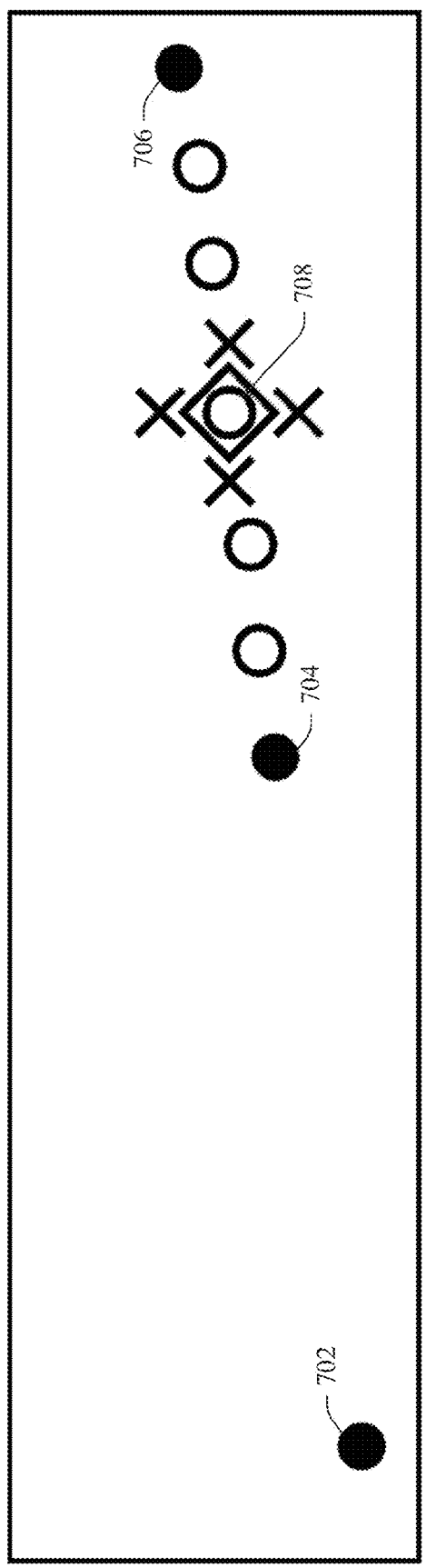
FIG. 7 illustrates a conceptual 2D diagram of temporal coherence techniques useable in aspects of the subject innovation.

FIG. 7 illustrates a conceptual 2D diagram of temporal coherence techniques useable in phase 1. Circles 702 and 704 represent the bone in the previous two solved frames. Circle 706 is the predicted point for the current frame. Intermediate circles represent the additional intermediate points. Circle 708 within the diamond represents the selected seed point. The cross points represent the surrounding regions which can be searched in the next phases.

The first phase used temporal coherence to find a good starting position for each bone. Using the position and orientation of a bone in the most recent two frames, the most likely area in the current frame to search for the optimal position and orientation was predicted (although in other aspects, a different number of most recent frames can be used). The positions of the previous two solved frames (circles 702 and 704 in FIG. 7) were extrapolated to predict the position in the current frame. Then the intermediate positions (intermediate circles in FIG. 7) were generated between the predicted position and the position of the closest solved frame. Finally, the best-match position among all these potential positions was found. The rationale of multiple intermediate points is that a bone can change its direction and speed of movement. Multiple intermediate points help to compensate for this variation in speed and direction. Subsequent phases thoroughly search the region surrounding a selected seed location (cross points in FIG. 7) in order to capture accelerated and decelerated motion. The intermediate seed points can be generated uniformly so that the translation difference or the angle difference between two consecutive seed points can be at most 0.5 mm or 0.50 degrees.

The sets $K_i$ and $L_i$ for this phase were: $K_i=\{B_i\}$ and $L_i=K_i$, where i=1:n.

Phase 2: Pairwise Optimization

The purpose of phase 2 was to refine the seed location from phase 1 with the help of adjacent bone location information. To this end, each pair of adjacent bones (e.g. B1-B2, B2-B3 and so on) was optimized in the hierarchy by optimizing over 12 degrees of freedom. Optimizing two adjacent bones simultaneously helps adjust their position and orientation with respect to each other. This optimization step is computationally tractable while providing the necessary and sufficient degrees of freedom between neighboring bones in order to adjust their relative position and orientation.

The sets $K_i$ and $L_i$ for this phase were: $K_i=\{B_i, B_{i+1}\}$ and $L_i=K_i$, where i=1:n−1.

Since bone kinematics are temporally smooth, the search space was further constrained by including motion priors into the optimization. The search range was restricted within twice (empirically determined) the magnitude of the bone motion in the most recent two frames. This motion prior allows sufficient freedom for bone movement but prevents sudden large movement. Theoretically, the search space could be further reduced by incorporating the fact that different bones cannot penetrate each other. While the computational cost of detecting 3D inter-penetration makes such an approach less desirable for the current implementation, this limitation can be overcome with future improvements in computational capabilities.

Phase 3: Biased Singleton Refinement

The purpose of this phase was to refine the position and orientation for each bone by searching in the region chosen by phase 2. It was noted that the bones of a hierarchy are unequally easy to track. For example, bones at the top (e.g. cervical vertebra C3 in a hierarchy of C3-C7) are easier to track due to less soft tissue and less interference from surrounding bones. The hierarchical search method can take advantage of this prior information by biasing the order in which individual bones are optimized. In the spine case, each bone of the chain was optimized sequentially (starting from the top of the chain and moving towards the bottom) in the presence of the previous bone in the hierarchy. Since one bone at a time was optimized, the optimization was over 6 degrees of freedom.

The sets $K_i$ and $L_i$ for this phase were: $K_i=\{B_1, \ldots, B_i\}$ and $L_i=\{B_i|B_1, \ldots, B_{i-1}$ are kept fixed$\}$, where i=1:n.

Phase 4: Neighbor-Constrained Refinement

Phase 4 was a refinement phase that worked similarly to phase 3, but took into account both predecessor and successor bones in the hierarchy. The movement of each bone during the optimization was restricted by the presence of all the surrounding bones of the hierarchy. This facilitated finding the optimal position and orientation for the whole hierarchy.

The sets $K_i$ and $L_i$ for this phase were: $K_i=\{B_1, \ldots, B_n\}$ and $L_i=\{B_i|B_1, \ldots, B_{i-1}, B_{i+1}, \ldots, B_n$ are kept fixed$\}$, where i=1:n.

Validation

To validate and evaluate the hierarchical, multi-bone approach, both in vivo conditions and real clinical data were used. 3D volumetric images of the bones of interest were obtained from a high resolution static computed tomography (CT) scanner (LightSpeed 16, GE Medical Systems, Waukesha, Wis.). CT images were segmented using 3D medical imaging software (Mimics, Materialize Inc, Leuven, Belgium) to extract individual bone geometry.

A Dynamic Stereo X-ray (DSX) system was used to capture high resolution X-ray images at a high frame rate. DSX utilizes two frame-synchronized imaging systems, specifically designed for dynamic measurement and mounted in a custom-designed, flexible positioning system to optimize viewing angles and provide freedom of subject movement. Each imaging system includes a 100 kW constant-potential high-frequency cardiac cine-radiographic generator (CPX-3100CV, EMD, Quebec, CA), a 0.3/0.6 mm focal spot size X-ray tube (G-1582; Varian, Salt Lake City, Utah), a 40 cm image intensifier (TH9447QX; Thales, France), and a high-speed camera providing 1800×2400 pixel resolution at up to 500 frames/sec with 14-bit dynamic range (Phantom V10; Vision Research, Inc., Wayne, N.J.). The EMD X-ray generators included upgraded software (provided by the manufacturer) to provide 1 ms pulses at repetition rates up to 180 Hz, providing blur-free images and a dose reduction of 4-16× (relative to continuous operation). A calibration object (an acrylic cube with metallic markers embedded in precisely known locations) was used to calibrate the camera system.

13 trials were acquired from 3 human subjects (1 male, 2 female, aged between 35-40)—3 flexion/extension and 3 axial rotation trials from subject 1 and 2 and 1 flexion/extension trial from subject 3. Two of the test subjects had single-level anterior fusion in C5 and C6 and the remaining subject has single-level anterior fusion in C4 and C5. A fusion is performed by attaching a metal plate with two vertebral bodies using 4 screws. Trials from the subjects were taken between 6 and 7 months post-surgery.

Tantalum beads were implanted into the fused cervical vertebrae and their adjacent bones during the fusion surgery so that a high accuracy ground truth solution could be produced by tracking the beads using standard stereo-photogrammetric methods. The subject with C4-5 fusion had beads into cervical vertebrae C3, C4, C5 and C6. Subjects with C5-6 fusion had beads into cervical vertebrae C4, C5, C6 and C7. Bead signatures were manually removed from the CT slices prior to MDRR generation by replacing voxels containing bead signatures with the average of the neighborhood voxels which do not belong to beads. In this way, the beads did not influence the hierarchical and the operator-assisted tracking methods. For validation purposes, the center of each bead was also manually identified in the CT scans.

For these subjects and trials, 5 cervical vertebrae (C3-C7) and the fusion hardware were tracked. In the clinical study that generated this data, cervical vertebrae C1 and C2 were not tracked, and so they did not have beads implanted into them to produce a ground truth solution. Table 1 shows additional specifications of the datasets:

TABLE 1

| Experiment data set specification | |
|---|---|
| Bone | Cervical Spine (C3-C7) |
| Motion | Flexion/extension, axial rotation |
| Total trials | 13 |
| Original CT Resolution(mm) | 0.23 × 0.23 × 1.25 |
| Interpolated CT resolution (mm) | 0.23 × 0.23 × (0.23~0.5) |
| X-ray image resolution | 1024 × 1024 |
| Number of frames per trial | 60~100 |
| Frame capturing rate | 30 frames/sec |
| Pixel size of x-ray image (mm) | 0.30 × 0.30 |

The ground truth was obtained by tracking the implanted beads in the distortion-corrected radiographs. To validate this ground truth, bias and precision were measured. In overview, first, inter-bead distances ($d_i$ where i is the frame number) were calculated per bone over an entire trial from the bead tracking (i.e., ground truth) results. True inter-bead distance (D) was measured by manually detecting the beads in the CT image. Next, differences between the inter-bead distance computed from the CT data and the bead tracking based solution ($D-d_i$) were calculated for each frame over an entire trial. Bias and precision were defined as the mean and standard deviation of the differences over the entire trial and were summarized over all trials to report in the form mean±standard deviation. Bead-based tracking was used as the "gold standard" to calculate the accuracy of the operator-assisted single-bone and hierarchical multi-bone tracking.

Performance of the operator-assisted single-bone and the hierarchical multi-bone methods were compared for each bone and each axis in terms of bias, precision, root-mean-squared (rms) error, and maximum error. These performance metrics were computed with respect to the bead-based ground truth solution. For each method (operator-assisted, ground truth, and hierarchical) the bead centroid locations were computed as the average of the three known bead coordinates of a bone over all frames of a trial. The differences between estimated bead centroid (hierarchical or operator-assisted method) and the ground truth bead centroid locations were computed for each bone and for each axis across all frames of a trial, infra. Bias, precision, rms error and maximum error were defined as the mean, standard deviation, rms value and maximum value of this time-history of differences. Finally, bias, precision and rms error are summarized below as the mean, standard deviation and maximum error over all trials. To further compare the performance of the operator-assisted and the hierarchical method for a bone along each axis direction, two sample t-tests ($\alpha=0.05$) were performed on bias, precision and rms error of the bone.

In the experiments discussed herein, the operator-assisted single-bone method was guided by an expert operator and the solution was checked and refined manually. The hierarchical method did not require any human assistance after initialization. The solutions from these two methods were compared in terms of accuracy, robustness and run time.

There was no bias in the implanted bead tracking solution shown in Table 2, i.e., in the ground truth.

TABLE 2

Bead-based tracking accuracy (bias and precision).

| Bone | Bias (mm) | Precision (mm) |
|---|---|---|
| C3 | 0.05 ± 0.03 | 0.11 ± 0.02 |
| C4 | 0.04 ± 0.03 | 0.10 ± 0.03 |
| C5 | −0.04 ± 0.10 | 0.12 ± 0.02 |
| C6 | 0.04 ± 0.07 | 0.12 ± 0.04 |
| C7 | 0.02 ± 0.05 | 0.08 ± 0.03 |

Average precision over all bones was 0.11 mm, which was very similar to earlier results.

The accuracy of the operator-assisted single-bone and the hierarchical multi-bone methods were compared in terms of bias, precision, rms error and maximum error for each bone along each axis direction, as shown in Table 3:

TABLE 3

Bias of the hierarchical method and the operator-assisted method. Mean ± standard deviation of bias over all trials

| Axis | Hierarchical multi-bone method | | | Operator-assisted single-bone method | | |
|---|---|---|---|---|---|---|
| | X (mm) | Y (mm) | Z (mm) | X (mm) | Y (mm) | Z (mm) |
| C3 | 0.04 ± 0.12 | 0.01 ± 0.17 | 0.08 ± 0.05 | −0.04 ± 0.17 | −0.04 ± 0.22 | 0.03 ± 0.08 |
| C4 | 0.07 ± 0.08 | 0.02 ± 0.15 | 0.18 ± 0.16 | −0.03 ± 0.13 | 0.05 ± 0.09 | 0.21 ± 0.14 |
| C5 | 0.19 ± 0.20 | 0.06 ± 0.39 | −0.07 ± 0.31 | 0.22 ± 0.18 | 0.11 ± 0.29 | −0.07 ± 0.42 |
| C6 | −0.08 ± 0.25 | −0.04 ± 0.10 | 0.07 ± 0.14 | 0.00 ± 0.49 | 0.12 ± 0.22 | 0.04 ± 0.14 |
| C7 | −0.18 ± 0.14 | −0.27 ± 0.06 | −0.12 ± 0.18 | −0.13 ± 0.06 | −0.16 ± 0.10 | 0.02 ± 0.07 |

Figure 8:
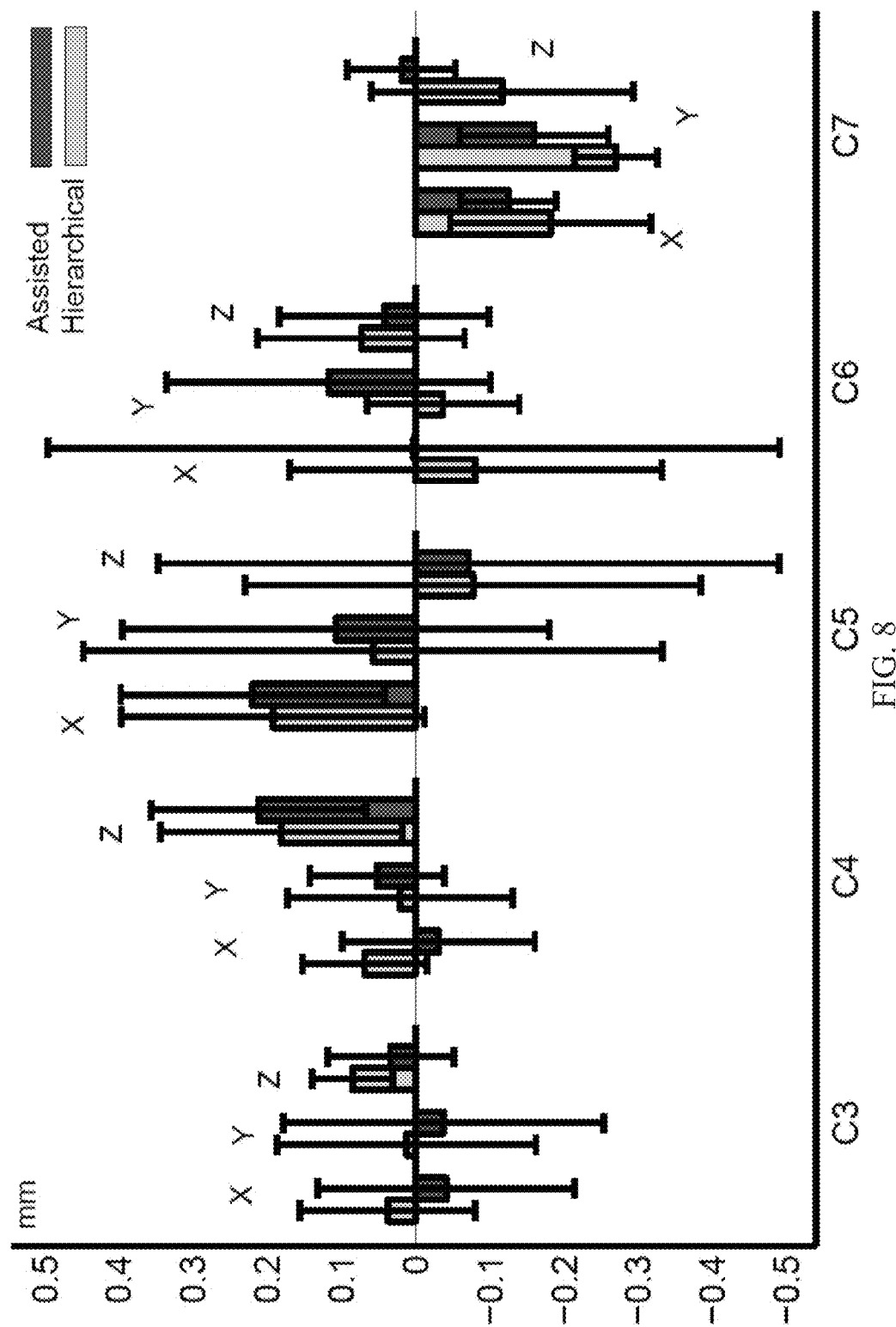
FIG. 8 shows a graph of the bias in the hierarchical multi-bone method and the operator-assisted single-bone method.

FIG. 8 shows a graph of the bias in the hierarchical multi-bone method and the operator-assisted single-bone method. The results were averaged over 13 trials from 3 subjects, with 60~100 frames per trial. As seen in Table 3 and FIG. 8, no statistically significant difference in bias (p>0.01) was found for any bone along any axis direction between the hierarchical and the operator-assisted method. This finding indicates that the hierarchical multi-bone method has similar accuracy to the operator-assisted single-bone method. C5 and C6 have relatively higher bias than C3, C4 and C7 along the X and Y axes both for the operator-assisted single-bone and the hierarchical methods. Maximum bias of C3, C4 and C7 using the operator-assisted single-bone method along the X and Y axes were approximately 7 and 3 times higher than the maximum bias of C5 and C6 using the same method along X and Y axes. In contrast, maximum bias of C3, C4 and C7 using the hierarchical multi-bone method along the X and Y axes was approximately 3 and 4 times higher than the maximum bias of C5 and C6 using the same method along the X and Y axes. C5 and C6 tracking results show relatively higher bias than other bones because C5 was fused in all three of our subjects and C6 was fused in two of our three subjects. Fused vertebrae are typically harder to track due to relatively inaccurate CT-scan models of the fused bones (extracting a CT bone model from fused vertebrae is more difficult than extracting a bone model from non-fused vertebrae), interference from hardware during tracking, etc. However, the bias for the hierarchical method for C5 and C6 along any axis was less than 0.62 mm; for the operator-assisted single-bone method it was less than 1.07 mm which indicates that the hierarchical multi-bone method has sub-millimeter accuracy for all vertebrae, including the ones which have been affected by fusion surgery.

Figure 9:
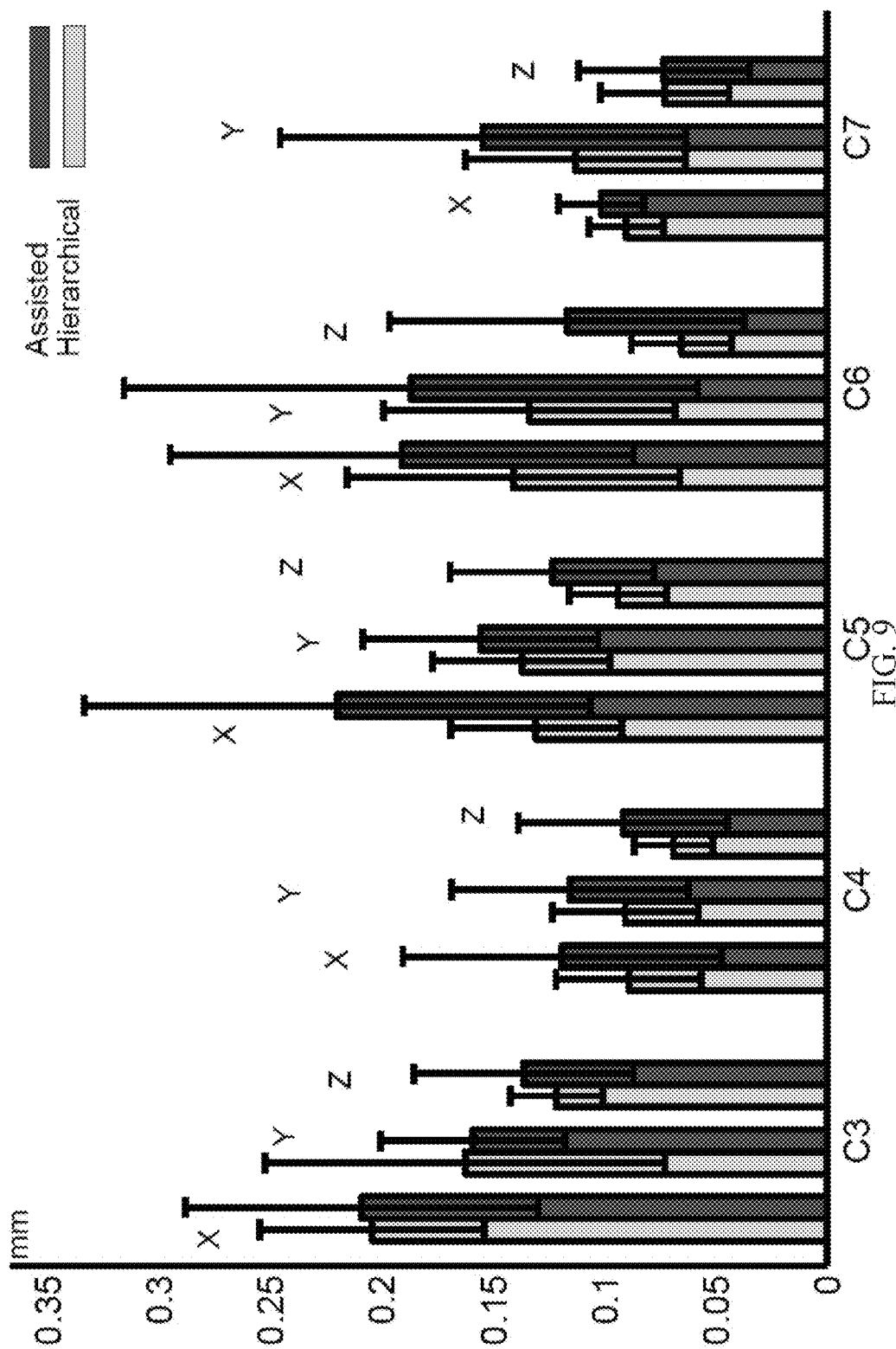
FIG. 9 shows a graph of a comparison of the precision of the hierarchical multi-bone method and the operator-assisted single-bone method.

FIG. 9 shows a graph of a comparison of the precision of the hierarchical multi-bone method and the operator-assisted single-bone method. Hierarchical multi-bone method precision ranged from 0.03 mm to 0.34 mm depending on axis direction. Operator-assisted single-bone method precision ranged from 0.04 mm to 0.55 mm depending on axis direction. No statistically significant difference (p>0.01) in precision between the hierarchical and the operator-assisted methods was found along any coordinate system direction, as seen in Table 4:

TABLE 4

Precision of the hierarchical method and the operator-assisted method. Mean ± standard deviation of precision over all trials

| Axis | Hierarchical multi-bone method | | | Operator-assisted single-bone method | | |
|---|---|---|---|---|---|---|
| | X (mm) | Y (mm) | Z (mm) | X (mm) | Y (mm) | Z (mm) |
| C3 | 0.20 ± 0.05 | 0.16 ± 0.09 | 0.12 ± 0.02 | 0.21 ± 0.08 | 0.16 ± 0.04 | 0.14 ± 0.05 |
| C4 | 0.09 ± 0.03 | 0.09 ± 0.03 | 0.07 ± 0.02 | 0.12 ± 0.07 | 0.12 ± 0.05 | 0.09 ± 0.04 |
| C5 | 0.13 ± 0.04 | 0.14 ± 0.04 | 0.09 ± 0.02 | 0.22 ± 0.11 | 0.16 ± 0.05 | 0.12 ± 0.05 |
| C6 | 0.14 ± 0.07 | 0.13 ± 0.07 | 0.07 ± 0.02 | 0.19 ± 0.10 | 0.19 ± 0.13 | 0.12 ± 0.08 |
| C7 | 0.09 ± 0.02 | 0.11 ± 0.05 | 0.07 ± 0.03 | 0.10 ± 0.02 | 0.15 ± 0.09 | 0.07 ± 0.04 |

Precision was bone-independent for both of the methods. The last bone to track (C7) shows slightly worse accuracy in the hierarchical method than in the operator-assisted single-bone method. A possible explanation is that C7s have more soft tissue surrounding them compared to other bones in the dataset. Therefore, the assumption of negligible contribution in pixel intensity due to surrounding soft tissue for MDRR generation (in equation 3) may no longer hold for C7, making human intervention particularly valuable. Additionally, the operator-assisted single-bone method C5 and C6 show slightly lower precision (statistically not significant) than C3, C4 and C7.

Figure 10:
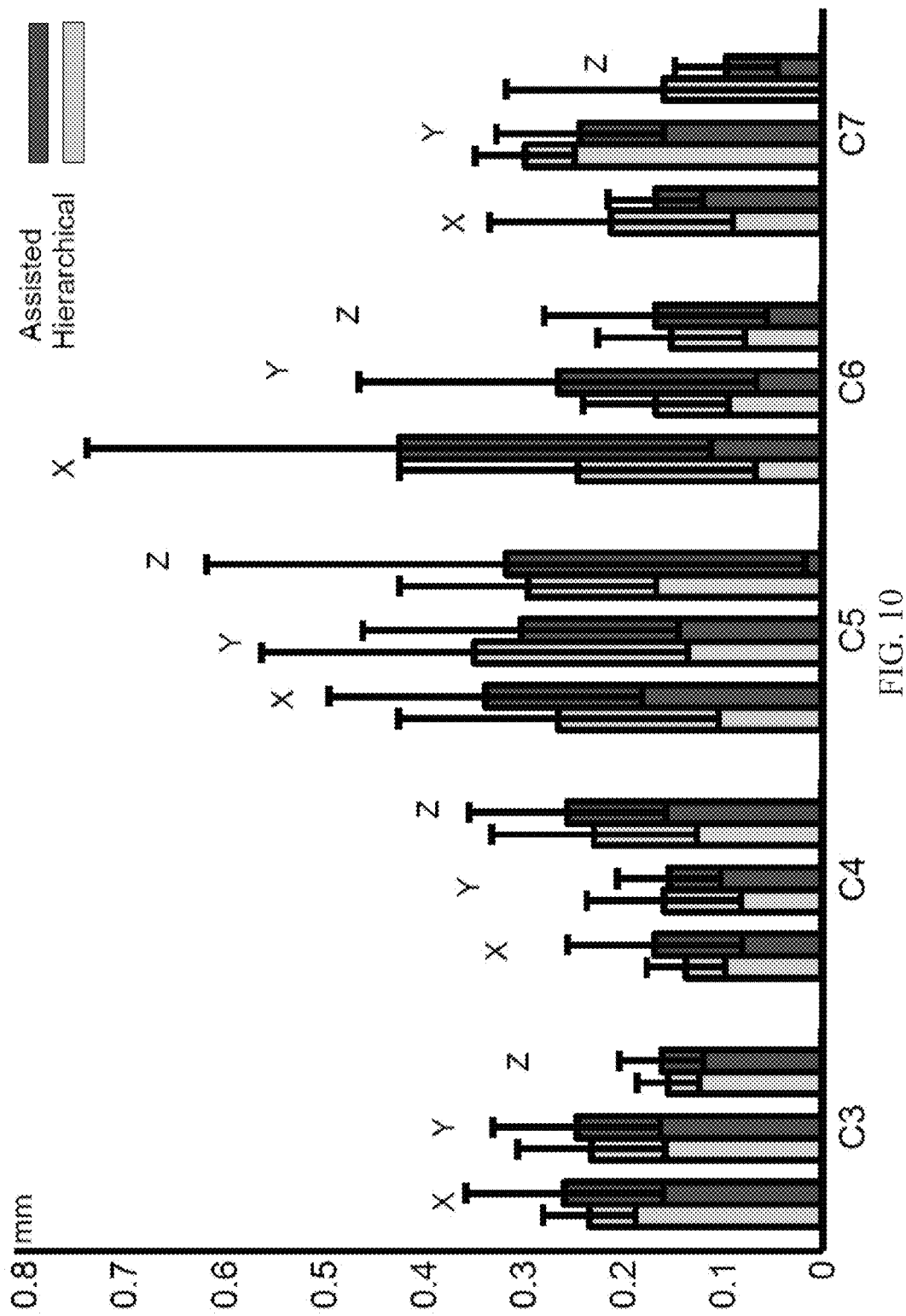
FIG. 10 shows a graph of the root-mean-squared (rms) error of the hierarchical and the operator-assisted methods.

FIG. 10 shows a graph of the root-mean-squared (rms) error of the hierarchical and the operator-assisted methods. Root-mean-squared error indicates no statistically significant difference (p>0.01) between the hierarchical and the operator-assisted methods for any bone in any coordinate system direction, as seen in Table 3:

| | Mean ± standard deviation of root-mean-squared error over all trials | | | | | |
|---|---|---|---|---|---|---|
| | Hierarchical multi-bone method | | | Operator-assisted single-bone method | | |
| Axis | X (mm) | Y (mm) | Z (mm) | X (mm) | Y (mm) | Z (mm) |
| C3 | 0.23 ± 0.05 | 0.23 ± 0.07 | 0.15 ± 0.03 | 0.26 ± 0.10 | 0.25 ± 0.08 | 0.16 ± 0.04 |
| C4 | 0.14 ± 0.04 | 0.16 ± 0.08 | 0.23 ± 0.10 | 0.17 ± 0.09 | 0.15 ± 0.05 | 0.26 ± 0.10 |
| C5 | 0.26 ± 0.16 | 0.35 ± 0.21 | 0.29 ± 0.13 | 0.37 ± 0.16 | 0.30 ± 0.16 | 0.32 ± 0.30 |
| C6 | 0.24 ± 0.18 | 0.17 ± 0.07 | 0.15 ± 0.07 | 0.42 ± 0.31 | 0.26 ± 0.20 | 0.17 ± 0.11 |
| C7 | 0.21 ± 0.12 | 0.30 ± 0.05 | 0.16 ± 0.16 | 0.17 ± 0.05 | 0.24 ± 0.08 | 0.10 ± 0.05 |

From FIG. 10, it can be seen that vertebrae C5 and C6 show slightly higher rms error than the vertebrae C3, C4 and C7 for the operator-assisted single-bone method. For the operator-assisted single-bone method, the maximum rms error was 1.11 mm for C5 and C6, and 0.44 mm for C3, C4 and C7. For the hierarchical multi-bone method, the maximum rms error was 0.70 mm for C5 and C6, and 0.51 mm for C3, C4 and C7. The rms error result again indicated that the hierarchical multi-bone method is as accurate as the operator-assisted single-bone method even for the vertebrae with fusion hardware.

Figure 11:
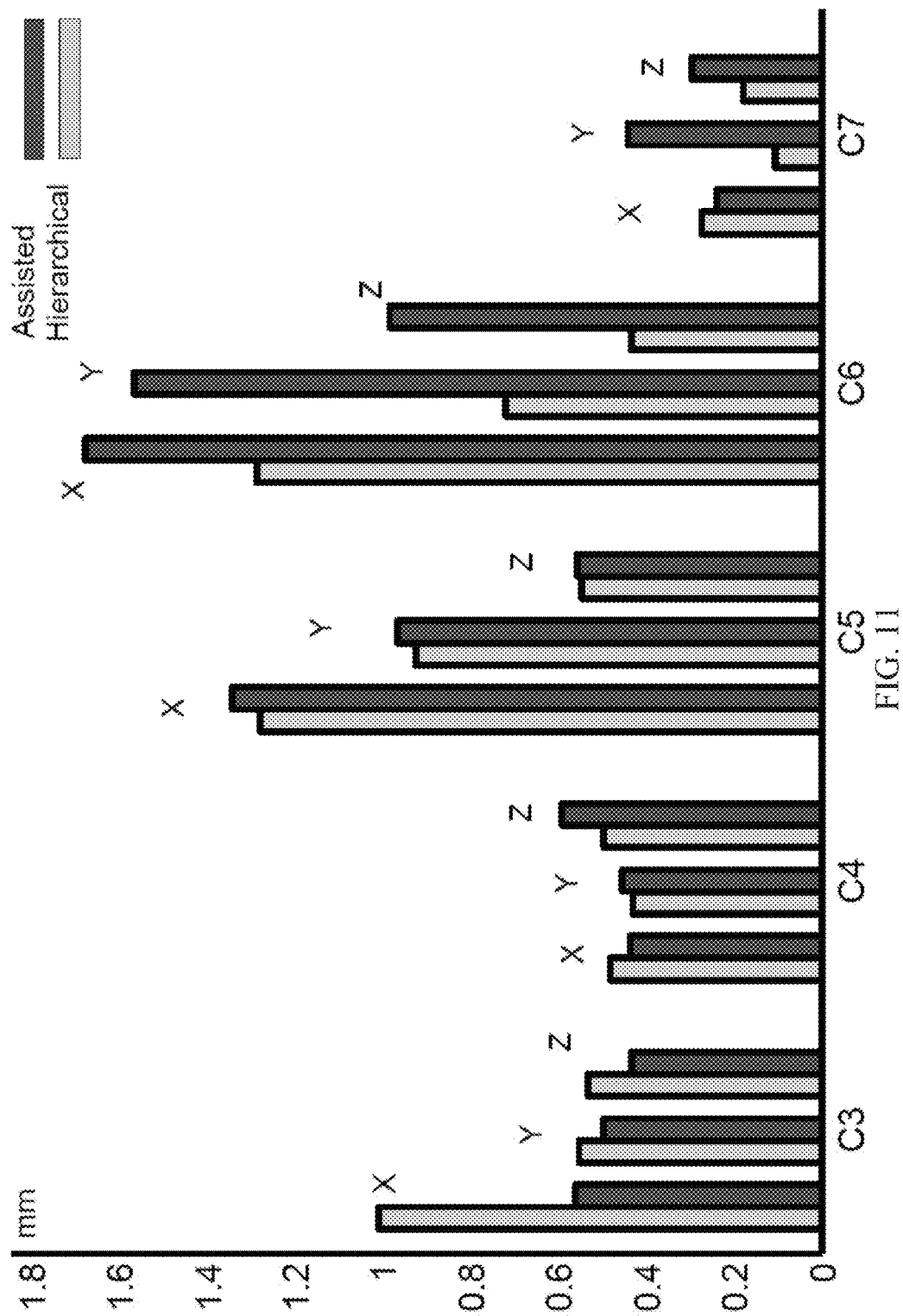
FIG. 11 shows a graph of the maximum error of the hierarchical and the operator-assisted method.

FIG. 11 shows a graph of the maximum error of the hierarchical and the operator-assisted method. Notably for both of the methods the maximum error was often greater than or close to 1 mm (especially for C5 and C6). Considering the sub-millimeter level values found in bias, precision and rms error analysis, these high values in maximum error analysis indicate the presence of outliers X-ray frames where the image quality is relatively poorer than most other frames. According to the expert operators, this is often the case, and the operator-assisted single-bone method fails mainly for these outlier frames. Table 6 shows the maximum error for both methods:

TABLE 6

Maximum error of the Hierarchical method and the operator-assisted method.

| | Maximum error | | | | | |
|---|---|---|---|---|---|---|
| | Hierarchical multi-bone method | | | Operator-assisted single-bone method | | |
| Axis | X (mm) | Y (mm) | Z (mm) | X (mm) | Y (mm) | Z (mm) |
| C3 | 1.01 | 0.55 | 0.53 | 0.56 | 0.50 | 0.43 |
| C4 | 0.48 | 0.43 | 0.50 | 0.43 | 0.45 | 0.59 |
| C5 | 1.28 | 0.93 | 0.55 | 1.34 | 0.97 | 0.56 |
| C6 | 1.28 | 0.72 | 0.43 | 1.68 | 1.57 | 0.99 |
| C7 | 0.27 | 0.11 | 0.18 | 0.24 | 0.44 | 0.30 |

A quantitative analysis of the implant hardware motion could not be performed due to the lack of a bead-based ground truth solution. However, two human expert operators manually checked the hierarchical method tracking solution of the implant hardware. According to the expert operators, the hierarchical method tracking solution of implant hardware was accurate and those experts often commented that the hierarchical tracking solution seemed better than the operator-assisted method tracking solution.

To further analyze the effect of implant hardware on method accuracy, the hierarchical method was used to track a trial (subject 1, flexion-extension trial 1) without including the implant hardware in the MDRR generation process. This approach produced a very poor quality solution for the fused vertebra C5, while the other fused vertebra C6 went off track around frame 15.

The hierarchical multi-bone approach was significantly more robust than the operator-assisted method. 13 trials were tracked from the 3 subjects. To compare the robustness of the hierarchical method with the single-bone method, these trials were tracked using the single-bone method without human operator assistance after initialization of the reference frames. The single-bone method failed to track 5 trials (3 flexion/extensions and 1 axial rotation from subject 1, 1 flexion/extension from subject 3). In all these trials, either vertebra C5 or C6 went significantly off track. For example, in the flexion/extension trial from subject 3, vertebra C6 went visibly off track around frame 6 and the bone remained off track for the rest of the frames. C6 also went off track in all 3 flexion/extension trials from subject 1 approximately around frame 10. C5 went off track in one axial rotation trial from subject 1 around frame 15. Although the single-bone method was able to complete tracking the remaining 8 trials, the tracking results required significant manual correction through human operator intervention.

A Windows based cluster with 24 Intel Xeon (2.0 GHz) processors was used to run both the operator-assisted and the hierarchical tracking methods. The operator-assisted single-bone method required approximately 1 hour to track a single cervical vertebra in a single trial of 60~90 frames, leading to a total of 6 hours for the five cervical vertebrae and the metallic implant. 96% of the time was spent on human interaction during the tracking (to keep bones on track) and the manual refinement phase. The hierarchical method tracked five cervical vertebrae and the metallic implant on average in approximately 25 minutes, i.e., it attained a speedup factor of 12. Since most of this time was computational, the reduction in human interaction time was even greater, and tracking time could be significantly further reduced using greater parallelization. While having a faster solution is not the only advantage of the subject innovation, these run times indicate the hierarchical method is cost-effective, which is essential for clinical application.

The experimental results show that the hierarchical multi-bone method matches the sub-millimeter accuracy of the state-of-the-art operator-assisted single-bone approach. At the same time, the hierarchical method is superior to the single-bone method in terms of robustness and run-time. Notably, the hierarchical approach dramatically reduces the labor required for imaging studies, while making the accuracy and robustness of the method operator-independent.

An advantage of the hierarchical method is that it is able to track bones that change both direction and speed within each camera view during a specific trial, a task significantly more difficult than tracking a bone that moves in the same direction at a constant speed. In the experiments discussed herein, no restrictions were imposed on the subjects during motion. The maximum range of motion was approximately 20 mm translation and 32° rotation; bone motion direction and speed had variations in all datasets.

In experiments discussed herein, post-operative CT scan data was used to extract a model of each hierarchy component to be tracked, be they vertebrae or additional hardware. However, a pre-operative CT scan can also be used with this approach. The pre-operative scan could be used to extract models of the bones; while the implant model can be acquired either through scanning or directly via CAD designs.

The experiments followed an incremental approach in developing the four step hierarchical searching process. For example, the initial searching process included only two steps (Phase 1 and 3), but did not produce as good of a solution for the first node of the hierarchy. Several other structures were tried for the hierarchical searching, e.g. different orderings of the phases and different orderings of the bones. These approaches did not produce any improvements over the approach described herein, although in various aspects, different orderings of phases and/or bones can be employed in connection with the subject innovation.

Furthermore, the hierarchical multi-bone method assumes that noise in X-ray images due to surrounding soft-tissue structure of cervical spine is negligible. However, it is often very challenging to avoid soft-tissue interference and get high quality noise-free X-ray images from both cameras of a DSX system due to restrictions imposed by a subject's motion and body structure. Various model-based techniques, including aspects of the subject innovation, can employ image filters as a pre-processing step to reduce noise due to soft tissue. Many of these image processing techniques require manual tuning even for a single dataset, primarily due to overall intensity variation from frame to frame. Adjusting these parameters for different datasets (or for different frames within the same dataset) can require human effort.

In experiments discussed herein, the performance of the hierarchical multi-bone method was compared against the operator-assisted single-bone method, which represents the current state of the art in the field. Biplane or stereo radiographic imaging similar to the one used in experiments discussed herein can enable accurate quantitative 3D motion assessment for both static and dynamic bone motion analysis. Bone location and orientation can be precisely measured by beads (Radiostereometric analysis or RSA) implanted into the bones; bead-based tracking has shown good accuracy and has been used to produce ground truth to validate other tracking methods. Other model-based methods are primarily single-2D to 3D matching (i.e. they only collect one x-ray view). Typically, motion is kept within a plane perpendicular to the direction of camera projection. A study on knee implant tracking reported out of plane translation errors greater than 3 mm despite the fact that the movement was mainly in plane. One study compared the accuracy of its method to others. To summarize, all matching that is done using only one X-ray view has large errors perpendicular to the imaging plane. This class of methods is highly unlikely to produce higher accuracy results than the biplane radiographic approach. Some other conventional techniques collect 2 X-ray views. They build bone models from MRI/CT and either manually match the model to the 2 X-ray views or use invasively implanted beads for the matching process. Given the fundamentally manual, respectively invasive matching processes used, these approaches are not preferable to either the expert-assisted method or the hierarchical method of the subject innovation described herein.

While experiments discussed herein used data acquired through a stereo-radiographic imaging system and a CT scanner, a variety of imaging hardware setups, including single-plane radiography, can be used in practice to acquire dynamic radiograph images. Stereo-imaging is more likely than single-plane radiography to suffer from image quality problems due to scatter radiation and thus tracking motion from stereo images is likely to benefit more from the approach of the subject innovation. However, radiographic bone overlap and temporal coherence are traits of both single-plane and stereo-imaging; the hierarchical tracking algorithm disclosed herein may enhance the accuracy and robustness of single-plane dynamic tracking. Accordingly, although stereo-imaging is discussed in greater detail herein, it is to be appreciated that the subject innovation can be employed in conjunction with single-plane imaging as well. A major advantage of the approach of the subject innovation is that, in the long run, it could eliminate the requirement for simultaneous image acquisition, thus leading to dramatic improvements in radiographic image quality.

In aspects, the subject innovation can comprise systems and methods that can employ an intelligent, hierarchical algorithm, which can improve the accuracy, reliability, and/or flexibility of the dynamic radiograph tracking process. Aspects of the subject innovation can employ one or more of the techniques described herein—such as multibone projection (MDRR), temporally-aware constrained hierarchical optimization, etc.—can be applied separately or in combination to enable rapid, automated, accurate bone motion tracking and to facilitate clinical application.

The subject innovation can be employed in a variety of settings, such as tracking motion of multi-articular joints, as well as other settings. When applied to cervical spine data, the algorithm matched the sub-millimeter accuracy of the expert-operator existing tracking process, while being automated and operator-independent. The approach was also more robust in the presence of implanted hardware than the previous state-of-the-art tracking process. Finally, the approach sped up the total tracking time by a factor of 12. Preliminary evaluation indicates similar improvements on in vitro lumbar spine data.

The automated process that can be employed in aspects of the subject innovation decreases the labor cost associated with human operators, which facilitates practical clinical application. Considering the relatively low levels of radiation involved by the imaging system (approximately half the amount of one cervical CT scan), the moderate hardware costs and the proliferation in recent years of biplane DSX systems, the automation of the tracking procedure according to aspects of the subject innovation shows promise for large-scale clinical application. Since the approach showed also good performance in the presence of implanted hardware, it can be used to study post-surgery cases and evaluate the effectiveness of a surgical intervention. Applications for this technology include (but are not limited to) assessment and diagnosis of musculoskeletal disorders, bone, ligament and joint injury, derangements of the spine and osteoarthritis.

In various aspects, several additional or alternative techniques, methods, and algorithms can be used in conjunction with the subject application.

In aspects based on simultaneous optimization of the entire 4D path or trajectory, the path can be determined via a parameter optimization problem, instead of the frame-by-frame approach discussed herein. A 4D parameter optimization technique that accommodates asynchronous image capture, such as used in conjunction with aspects of the subject innovation, has multiple advantages. It exploits temporal coherence in the data, which guarantees smooth transition between successive poses and enforces reasonable motion physics. Also, the integration of 3D motion capture data as a first approximation to the parameter estimation problem reduces the risk of the solution diverging uncontrollably. Moreover, the approach allows asynchronous capture of the x-ray images, which can greatly reduce image noise from x-ray scatter due to simultaneous acquisition. For asynchronous equipment without timing capabilities, timing could be obtained by a basic microcontroller system that digitally sampled simple x-ray detectors placed in the fringe of the field of view. Furthermore, it can be used in conjunction with a wider range of imaging devices. While only a few laboratories have synchronized biplanar video radiography systems, there are hundreds of labs and clinical sites that have asynchronous biplanar fluoroscopy units. An additional advantage is that the algorithms can be extended to single-plane fluoroscopy without substantial modification (albeit with reduced accuracy), allowing thousands of clinical imaging facilities to employ such aspects of the subject innovation without the need for more specialized imaging equipment.

In various aspects, one or more additional techniques and calibration methods can be employed, including techniques to address issues such as camera lens distortions, camera system calibration, image data reduction, and integrated marker tracking. Aspects that incorporate such techniques into the hierarchical algorithms of the subject innovation can better cope with image corruption due to overlap of multiple bones in a radiographic view. Additionally, various aspects of the subject innovation can incorporate joint-specific motion constraints to further improve algorithm robustness. In some aspects, the subject innovation can employ a Bayesian probabilistic position and orientation (pose) estimation algorithm that casts the pose estimation problem in the general framework of probabilistic inference and allows for the fusion of the dynamic stereo X-ray (DSX) system with a traditional motion capture system. In this Bayesian framework, the estimation of any given bone can be expressed as the product of the probability of the measured pose from the DSX system (the Bayesian Likelihood) and the probability pose obtained from an external optical motion capture system (the Prior).

In various aspects, differing optimization methods can be used than the quasi-Newton optimization method discussed supra, as quasi-Newton methods can be susceptible to some potential drawbacks. First quasi-Newton methods can sometimes find locally optimal but incorrect solutions. Second, quasi-Newton methods can be ill-suited for applying boundary conditions that limit the degrees of freedom to anatomically realistic values. Third, quasi-Newton methods do not lend themselves well to parallel processing, which could otherwise greatly speed up optimization.

In some aspects, simulated annealing or other parameter optimization techniques can be employed as an optimization method in conjunction with the subject innovation. Because simulated annealing algorithms are based on temperature reduction models from thermodynamics rather than gradient based methods, they lend themselves well to boundary condition problems, and have proven to be effective in movement simulations and well-suited for solving optimization problems such as maximization of expression 8. In some aspects, a parallel implementation of simulated annealing can be employed, such as simulated parallel annealing within a neighborhood (SPAN), as is known in the art.

Figure 12:
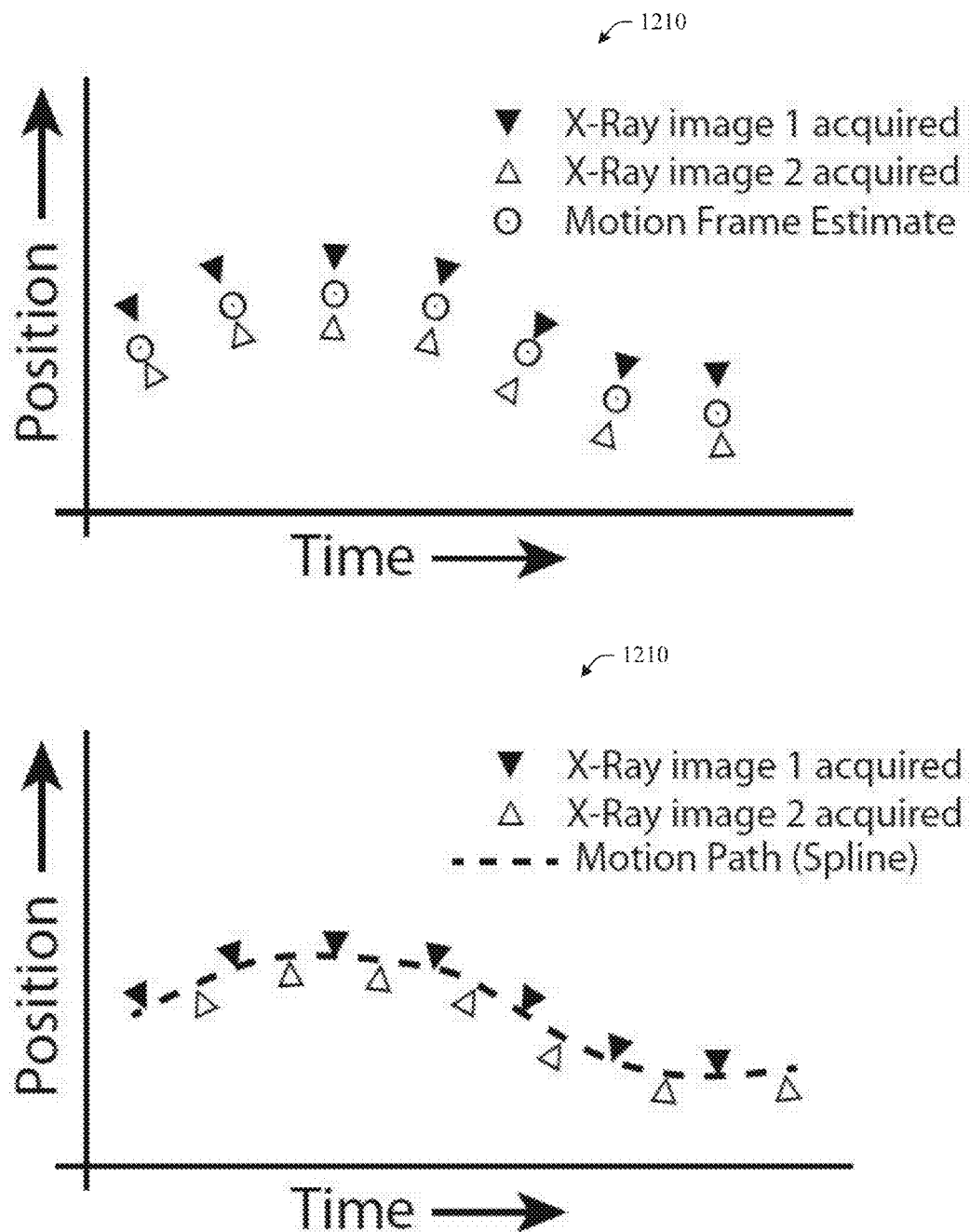
FIG. 12 illustrates the timing and utilization of image acquisition for determining bone pose in accordance with various aspects of the innovation.

Additionally, in some aspects, instead of solving on a frame-by-frame basis, expression 8 can be optimized to solve for all frames simultaneously. The extension to the optimization for 4D (3 dimensional space plus time) is that the generalized coordinates, q, of the transformation are defined by parametric curve (e.g., spline, etc.) functions consisting of n nodes that define the trajectory of the transformation across all frames. The continuous curve of the motion of the bone or bones of interest can be represented by a spline (e.g., Bezier spline, etc.) defined by a series of nodes. The parameter optimization can compute a small set of nodes distributed (e.g., evenly, etc.) across the frames of motion capture data, rather than the q's at all frames. This approach is demonstrated in FIG. 12, which illustrates the timing and utilization of image acquisition for determining bone pose. Representation 1210 shows the frame-by-frame approach, where images are obtained simultaneously, and each image pair is used independently to estimate the motion at a single frame. Representation 1220 diagrams the 4D tracking approach, which uses information from each image in a global optimization to estimate the entire motion path. One notable advantage of this approach is that it does not require that each DRR (e.g., SDRR or MDRR) be synchronized in time, only that a time stamp is available for determining the location in time on the spline function. Use of alternating images dramatically reduces image noise from radiation scatter, and can also increase temporal resolution for the same sampling rate (and radiation exposure for pulsed imaging). For asynchronous equipment without timing capabilities, timing could be obtained in a variety of ways, for example, by a basic microcontroller system that digitally samples simple x-ray detectors placed in the fringe of the field of view. Although a specific example of a solution via spline functions was discussed herein, it is to be understood that this example was solely for the purpose of illustration, and that other parametric curve techniques can also be utilized in various embodiments.

These algorithms (simulated annealing, optimization via parametric curves such as splines, etc.) are well suited to parallel processing. With the advent of moderately priced graphics processor units that continue to improve, computation time is becoming less and less relevant. Although these algorithms can potentially reduce computational time, they can also reduce manual user intervention time. Reducing the manual user intervention time can provide multiple advantages, such as reducing costs and allowing professionals more time to work on similar or different tasks.

Figure 13:
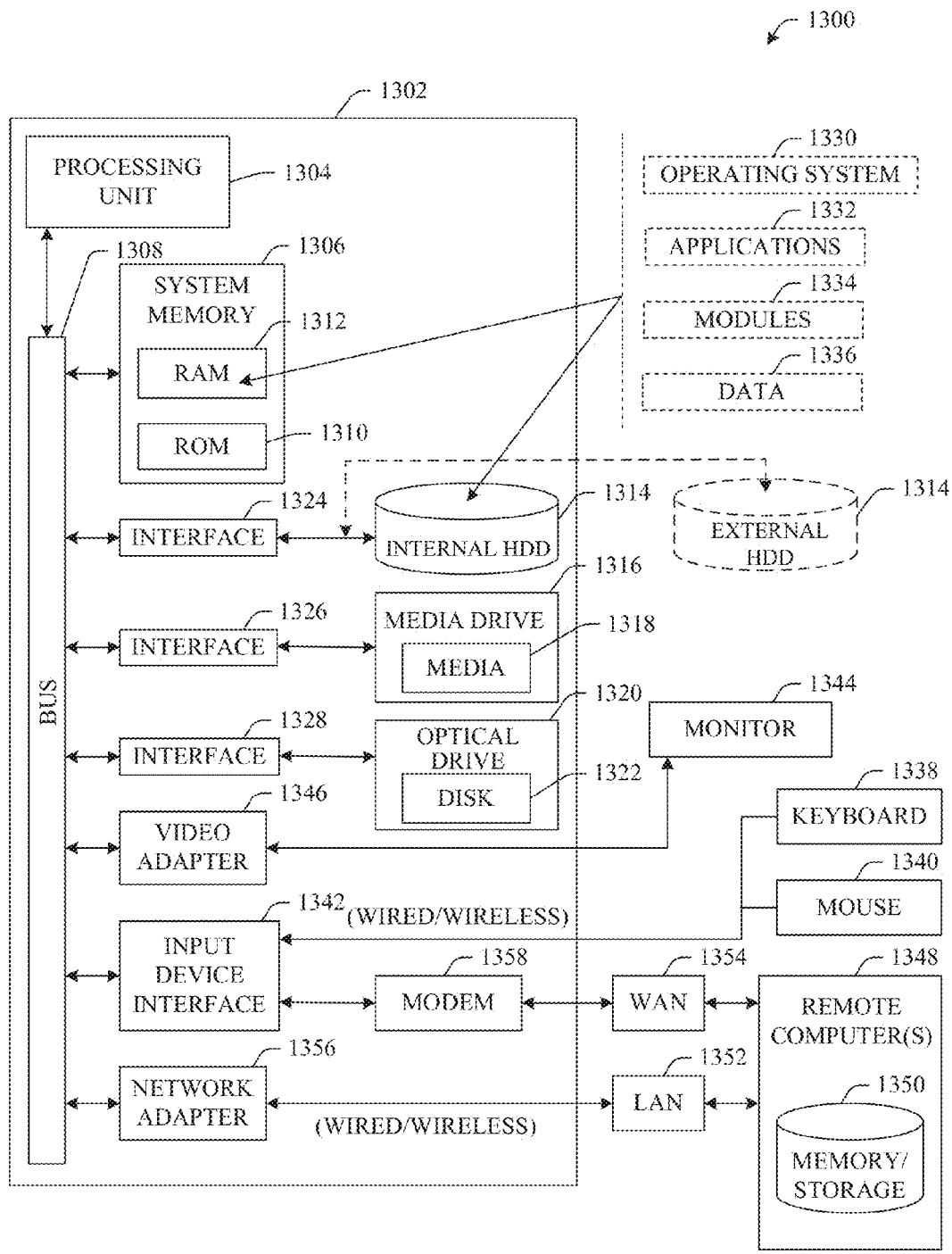
FIG. 13 illustrates a block diagram of a computer operable to execute the disclosed architecture.

Referring now to FIG. 13, there is illustrated a block diagram of a computer operable to execute the disclosed architecture. In order to provide additional context for various aspects of the subject innovation, FIG. 13 and the following discussion are intended to provide a brief, general description of a suitable computing environment 1300 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 13, the exemplary environment 1300 for implementing various aspects of the innovation includes a computer 1302, the computer 1302 including a processing unit 1304, a system memory 1306 and a system bus 1308. The system bus 1308 couples system components including, but not limited to, the system memory 1306 to the processing unit 1304. The processing unit 1304 can be any of various commercially available processors. Dual microprocessors and other multi-processor architectures may also be employed as the processing unit 1304.

The system bus 1308 can be any of several types of bus structure that may further interconnect to a memory bus (with or without a memory controller), a peripheral bus, and a local bus using any of a variety of commercially available bus architectures. The system memory 1306 includes read-only memory (ROM) 1310 and random access memory (RAM) 1312. A basic input/output system (BIOS) is stored in a non-volatile memory 1310 such as ROM, EPROM, EEPROM, which BIOS contains the basic routines that help to transfer information between elements within the computer 1302, such as during start-up. The RAM 1312 can also include a high-speed RAM such as static RAM for caching data.

The computer 1302 further includes an internal hard disk drive (HDD) 1314 (e.g., EIDE, SATA), which internal hard disk drive 1314 may also be configured for external use in a suitable chassis (not shown), one or more removable media drives 1316, (e.g., to read from or write to removable media 1318) and an optical disk drive 1320 (e.g., reading a CD-ROM disk 1322 or, to read from or write to other high capacity optical media such as DVD or Blu-Ray). The hard disk drive 1314, magnetic disk drive 1316 and optical disk drive 1320 can be connected to the system bus 1308 by a hard disk drive interface 1324, a magnetic disk drive interface 1326 and an optical drive interface 1328, respectively. The interface 1324 for external drive implementations includes at least one or more of Universal Serial Bus (USB), IEEE 1394, eSATA and Thunderbolt interface technologies or future interfaces. Other external drive connection technologies (including solid-state drives) are within contemplation of the subject innovation.

The drives and their associated computer-readable media provide nonvolatile storage of data, data structures, computer-executable instructions, and so forth. For the computer 1302, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 1312, including an operating system 1330, one or more application programs 1332, other program modules 1334 and program data 1336. All or portions of the operating system, applications, modules, and/or data can also be cached in the RAM 1312. It is appreciated that the innovation can be implemented with various commercially available operating systems or combinations of operating systems.

A user can enter commands and information into the computer 1302 through one or more wired/wireless input devices, e.g., a keyboard 1338 and a pointing device, such as a mouse 1340. Other input devices (not shown) may include a microphone, an IR remote control, a joystick, a game pad, a stylus pen, touch screen, or the like. These and other input devices are often connected to the processing unit 1304 through an input device interface 1342 that is coupled to the system bus 1308, but can be connected by other interfaces, such as a parallel port, an IEEE 1394 serial port, a game port, a USB port, an IR interface, etc. Gesture-based and/or three-dimensional input devices could also be incorporated to facilitate image/object manipulation.

A monitor 1344 or other type of display device is also connected to the system bus 1308 via an interface, such as a video adapter 1346. Three-dimensional display technologies could also be employed for enhanced visualization of bone tracking. In addition to the monitor 1344, a computer typically includes other peripheral output devices (not shown), such as speakers, printers, etc.

The computer 1302 may operate in a networked environment using logical connections via wired and/or wireless communications to one or more remote computers, such as a remote computer(s) 1348. The remote computer(s) 1348 can be a workstation, a server computer, a router, a personal computer, portable computer, microprocessor-based entertainment appliance, a peer device or other common network node, and typically includes many or all of the elements described relative to the computer 1302, although, for purposes of brevity, only a memory/storage device 1350 is illustrated. The logical connections depicted include wired/wireless connectivity to a local area network (LAN) 1352 and/or larger networks, e.g., a wide area network (WAN) 1354. Such LAN and WAN networking environments are commonplace in offices and companies, and facilitate enterprise-wide computer networks, such as intranets, all of which may connect to a global communications network, e.g., the Internet.

When used in a LAN networking environment, the computer 1302 is connected to the local network 1352 through a wired and/or wireless communication network interface or adapter 1356. The adapter 1356 may facilitate wired or wireless communication to the LAN 1352, which may also include a wireless access point disposed thereon for communicating with the wireless adapter 1356.

When used in a WAN networking environment, the computer 1302 can include a modem 1358, or is connected to a communications server on the WAN 1354, or has other means for establishing communications over the WAN 1354, such as by way of the Internet. The modem 1358, which can be internal or external and a wired or wireless device, is connected to the system bus 1308 via the serial port interface 1342. In a networked environment, program modules depicted relative to the computer 1302, or portions thereof, can be stored in the remote memory/storage device 1350. It will be appreciated that the network connections shown are exemplary and other means of establishing a communications link between the computers can be used.

The computer 1302 is operable to communicate with any wireless devices or entities operatively disposed in wireless communication, e.g., a printer, scanner, desktop and/or portable computer, portable data assistant, smartphone, tablet, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10 BaseT wired Ethernet networks used in many offices.

Figure 14:
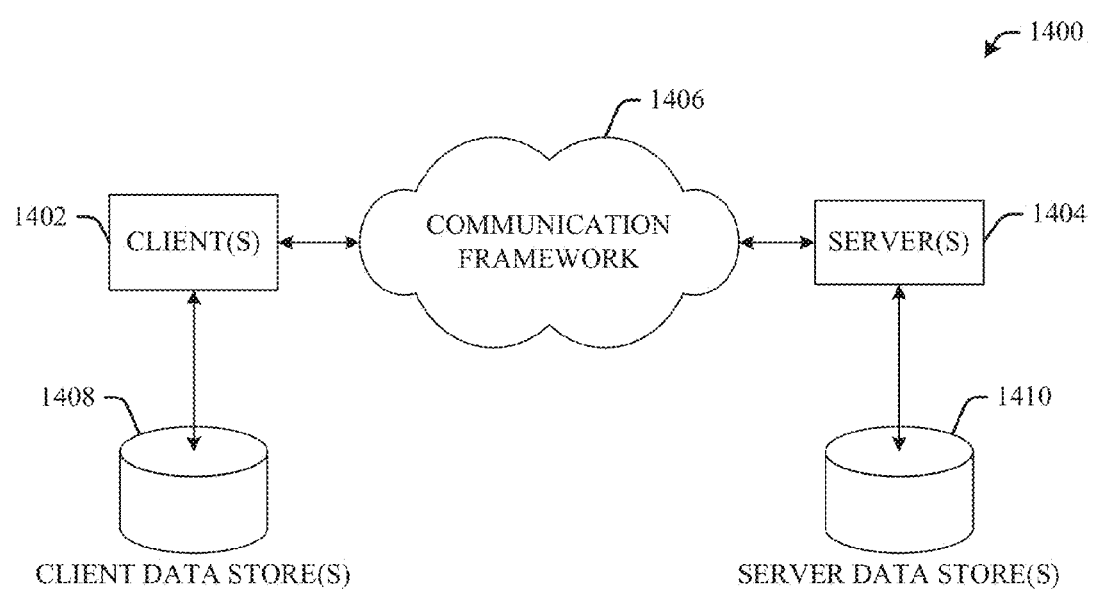
FIG. 14 illustrates a schematic block diagram of an exemplary computing environment in accordance with the subject innovation.

Referring now to FIG. 14, there is illustrated a schematic block diagram of an exemplary computing environment 1400 in accordance with the subject innovation. The system 1400 includes one or more client(s) 1402. The client(s) 1402 can be hardware and/or software (e.g., threads, processes, computing devices). The client(s) 1402 can house cookie(s) and/or associated contextual information by employing the innovation, for example.

The system 1400 also includes one or more server(s) 1404. The server(s) 1404 can also be hardware and/or software (e.g., threads, processes, computing devices). The servers 1404 can house threads to perform transformations by employing the innovation, for example. One possible communication between a client 1402 and a server 1404 can be in the form of a data packet adapted to be transmitted between two or more computer processes. The data packet may include a cookie and/or associated contextual information, for example. The system 1400 includes a communication framework 1406 (e.g., a global communication network such as the Internet) that can be employed to facilitate communications between the client(s) 1402 and the server(s) 1404.

Communications can be facilitated via a wired (including optical fiber) and/or wireless technology. The client(s) 1402 are operatively connected to one or more client data store(s) 1408 that can be employed to store information local to the client(s) 1402 (e.g., cookie(s) and/or associated contextual information). Similarly, the server(s) 1404 are operatively connected to one or more server data store(s) 1410 that can be employed to store information local to the servers 1404.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that facilitates modeling a motion of a bone, comprising:
    a processor operatively coupled to a memory, the memory comprising:
        a three dimensional (3D) model of the bone and one or more neighboring bones; and
        a sequence of frames of the motion of the bone, wherein each frame comprises one or more X-ray images of the bone and the one or more neighboring bones;
    a multi-bone digitally reconstructed radiograph (MDRR) generation component that generates one or more MDRRs corresponding to the motion of the bone, wherein each MDRR is a two-dimensional projection of the 3D model of the bone and the one or more neighboring bones based at least in part on one or more motion parameters, wherein the one or more motion parameters comprise an estimated bone position and orientation; and an optimization component that determines a set of optimal motion parameters for the sequence based on a comparison between the one or more MDRRs with the one or more X-ray images of at least one frame according to an objective function, wherein the one or more optimal motion parameters are the one or more motion parameters when the comparison maximizes the objective function, and wherein, when the comparison does not maximize the objective function, the optimization component adjusts the one or more motion parameters, the MDRR generation component generates one or more additional MDRRs based at least in part on the one or more adjusted parameters, and the optimization component compares the one or more additional MDRRs with the one or more X-ray images of the at least one frame according to the objective function.

2. The system of claim 1, wherein the MDRR generation component generates the one or more MDRRs based at least in part on one or more overlaps between the bone and the one or more neighboring bones.

3. The system of claim 1, wherein the MDRR generation component generates the one or more MDRRs based at least in part on one or more implants associated with the bone or the one or more neighboring bones.

4. The system of claim 1, wherein the MDRR generation component employs the estimated bone position and orientation and anatomical information to estimate x-ray absorption from one or more of soft tissue effects or scatter effects.

5. The system of claim 1, wherein the optimization component employs a coarse-to-smooth tracking hierarchy to progress from one or more fast approximations to the set of optimal motion parameters.

6. The system of claim 1, wherein the optimization component employs a tracking hierarchy associated with the bone and the one or more neighboring bones, and determines the set of optimal motion parameters for the sequence based at least in part on the tracking hierarchy.

7. The system of claim 6, wherein the tracking hierarchy is ordered based on an extent of overlap between the bone and the one or more neighboring bones.

8. The system of claim 1, wherein the one or more motion parameters are generated and adjusted based at least in part on a set of anatomical constraints defined between the bone and the one or more neighboring bones.

9. The system of claim 1, wherein the optimization component determines the set of optimal parameters on a frame-by-frame basis based at least in part on temporal coherence of the motion.

10. The system of claim 1, wherein the optimization component simultaneously determines the set of optimal parameters for each frame of the sequence.

11. The system of claim 10, wherein the optimization component determines the set of optimal parameters based at least in part on representing the entire sequence by a parametric curve.

12. The system of claim 11, wherein the optimization component determines the set of optimal parameters based at least in part on a parameter optimization algorithm.

13. The system of claim 1, wherein initial estimates of one or more motion parameters are based at least in part on motion data captured via an auxilliary measurement system utilizing optical, inertial or other non-radiographic methods.

14. A method that facilitates model-based tracking of a motion of a bone, comprising:

receiving, with a processor, a three-dimensional (3D) model of the bone and one or more neighboring bones;

receiving a sequence of frames corresponding to the motion of the bone, wherein each frame comprises one or more X-ray images;

receiving motion parameters comprising at least an estimate of position and an estimate of orientation for at least one frame of the sequence of frames;

generating one or more multi-bone digitally reconstructed radiographs (MDRRs) based at least in part on the motion parameters, wherein each MDRR is a two-dimensional projection of the 3D model of the bone and the one or more neighboring bones;

comparing the one or more MDRRs to the one or more X-ray images according to a similarity measure;

determining whether the motion parameters are optimized based at least in part on the comparing;

when the motion parameters are not optimized, adjusting the motion parameters and repeating the steps of generating, comparing, and determining based at least in part on the adjusted motion parameters; and outputting the motion parameters when the motion parameters are optimized.

15. The method of claim 14, wherein receiving motion parameters comprises:

receiving motion data captured via an auxilliary measurement system; and generating the estimate of position and the estimate of orientation based at least in part on the received motion data.

16. The method of claim 14, wherein generating the one or more MDRRs is based at least in part on an intensity contribution from the one or more neighboring bones.

17. The method of claim 14, wherein the steps of comparing, determining, and adjusting are performed for each frame of the sequence simultaneously.

18. The method of claim 17, wherein the steps of comparing, determining, and adjusting are based at least in part on a parameter optimization technique.

19. The method of claim 14, wherein the estimate of position and the estimate of orientation are based at least in part on one or more anatomical constraints on the bone and a physical relationship of the bone with the one or more neighboring bones.

20. A system that facilitates modeling a motion of a bone, comprising:

means for receiving a three dimensional (3D) model of the bone and one or more neighboring bones;

means for capturing a sequence of frames of the motion of the bone, wherein each frame comprises one or more X-ray images of the bone and the one or more neighboring bones;

means for generating one or more multi-bone digitally reconstructed radiographs (MDRRs) corresponding to the motion of the bone, wherein each MDRR is a two-dimensional projection of the 3D model of the bone and the one or more neighboring bones based at least in part on one or more estimated motion parameters; and means for optimizing the one or more estimated motion parameters based at least in part on a comparison between the one or more MDRRs and the one or more X-ray images.

* * * * *